US007842475B2

(12) United States Patent
Zheng et al.

(10) Patent No.: US 7,842,475 B2
(45) Date of Patent: Nov. 30, 2010

(54) STABILIZATION OF SOLID SUPPORT ASSAY REAGENTS

(75) Inventors: Yi Feng Zheng, Wilmington, DE (US); Tie Q. Wei, Bear, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 5 days.

(21) Appl. No.: 11/970,658

(22) Filed: Jan. 8, 2008

(65) Prior Publication Data
US 2009/0176213 A1    Jul. 9, 2009

(51) Int. Cl.
G01N 33/53    (2006.01)

(52) U.S. Cl. ............... 435/7.5; 435/7.1; 435/283.1; 435/287.2; 435/287.9; 436/518; 436/524; 436/527

(58) Field of Classification Search ........ 436/518, 436/524, 527; 435/7.1, 7.5, 283.1, 287.1, 435/287.2, 287.9
See application file for complete search history.

(56) References Cited

U.S. PATENT DOCUMENTS

| | | | |
|---|---|---|---|
| 4,496,654 A * | 1/1985 | Katz et al. ............ 435/7.5 |
| 5,026,653 A | 6/1991 | Lee et al. |
| 5,126,241 A | 6/1992 | Schenk |
| 5,332,679 A | 7/1994 | Simons et al. |
| 5,484,701 A | 1/1996 | Cocuzza et al. |
| 5,504,091 A | 4/1996 | Molnar-Kimber et al. |
| 5,690,907 A | 11/1997 | Lanza et al. |
| 5,770,459 A | 6/1998 | Massey et al. |
| 5,876,935 A * | 3/1999 | Pankratz et al. .......... 435/6 |
| 5,973,124 A | 10/1999 | Bayer et al. |
| 6,048,736 A * | 4/2000 | Kosak ............... 436/536 |
| 6,136,549 A * | 10/2000 | Feistel ............... 435/7.1 |
| 6,153,442 A | 11/2000 | Pirio et al. |
| 6,274,325 B1 | 8/2001 | Deger et al. |
| 6,881,536 B1 | 4/2005 | Shah et al. |
| 7,090,993 B2 | 8/2006 | Brady et al. |
| 7,101,682 B2 | 9/2006 | Ullman et al. |
| 7,105,311 B2 | 9/2006 | Kovalenko |
| 7,399,831 B2 * | 7/2008 | Lee et al. ............ 530/350 |
| 7,556,928 B2 * | 7/2009 | Jespersen et al. ........ 435/7.1 |
| 2001/0055766 A1 | 12/2001 | Aristarkhov et al. |
| 2002/0132231 A1 | 9/2002 | Collins |
| 2005/0118727 A1 | 6/2005 | Schelp |

(Continued)

*Primary Examiner*—Melanie Yu
(74) *Attorney, Agent, or Firm*—Theodore J. Leitereg

(57) ABSTRACT

Reagents are disclosed for use in assays for analytes. The reagents are dry assay reagents that may be readily reconstituted for use in the assays. The dry assay reagents comprise a solid support and one or more molecules of a receptor immobilized on the solid support. The receptor comprises one or more binding sites for a ligand. A portion of a total number of the binding sites is bound to a conjugate comprising the ligand linked to a specific binding pair member and a portion of the total number of the binding sites is free. In use in an assay, a combination is provided in an aqueous medium comprising the sample and reagents for detecting the analyte wherein at least one of the reagents comprises the dry assay reagent mentioned above. The combination is incubated under conditions for binding of the analyte to one or more of the reagents. The presence and/or amount of binding of the analyte to one or more of the reagents is detected where the presence and/or amount of the binding is related to the presence and/or amount of the analyte in the sample.

17 Claims, 13 Drawing Sheets

Scheme 4

U.S. PATENT DOCUMENTS

2005/0255460 A1 11/2005 Lu et al.
2006/0160151 A1 7/2006 Allred et al.
2006/0246518 A1 11/2006 Chen et al.
2006/0275820 A1 12/2006 Watkins et al.

* cited by examiner

Figure 1. Structures of CsA and CsC

Cyclosporine A (CsA) : R = H (1);
Cyclosporine C (CsC) : R = OH (2);

Scheme 1

Scheme 2

Scheme 3

Scheme 4

Scheme 5

Figure 7A. Structure of *anti*-CsA-*m*-Ab-LC-Biotin
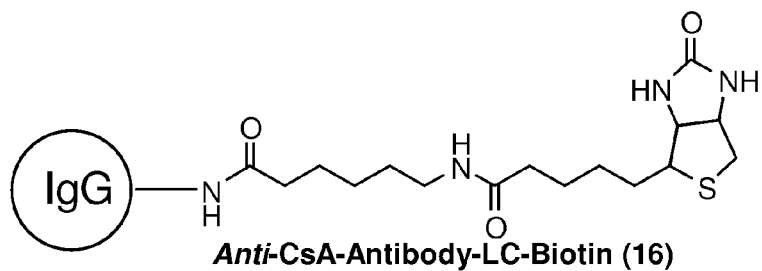
***Anti*-CsA-Antibody-LC-Biotin (16)**
Figure 7B. Structure of anti-CsA-m-Ab-PEO$_4$-Biotin
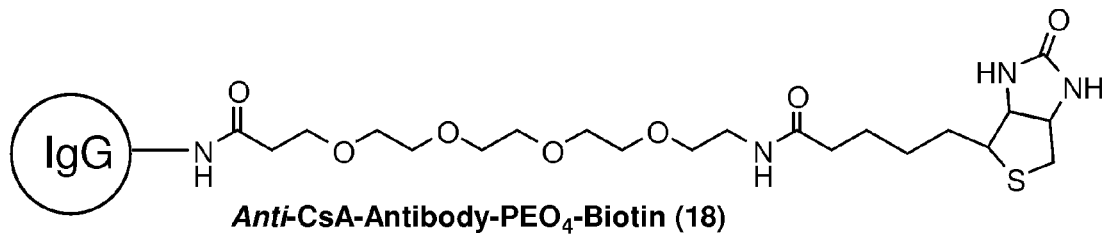
***Anti*-CsA-Antibody-PEO$_4$-Biotin (18)**
Figure 8
*Anti*-CsA-Antibody-EPRM Chemibead
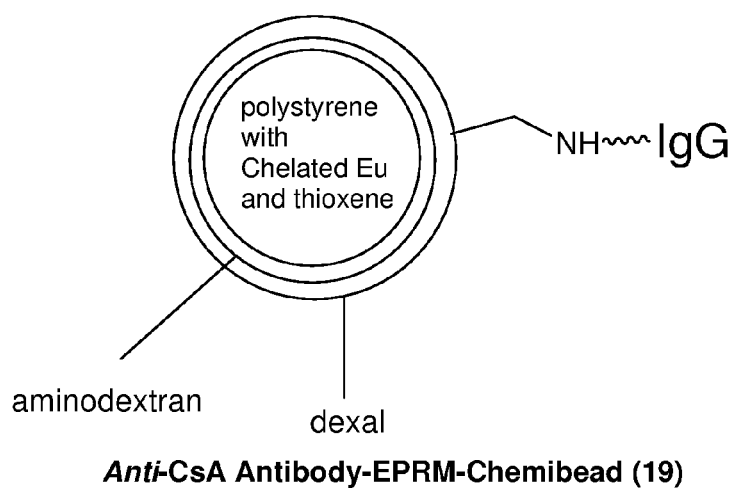
***Anti*-CsA Antibody-EPRM-Chemibead (19)**

Structure of CsA-DA-10-Bis-Biotin (31)

\* one isomer has same linker linking through this nitrogen

Scheme 6. Immobilization of *anti*-CsA antibody to EPRM.

Scheme 7. Synthesis of Bis-Biotin-Linker (26)

Scheme 8. Synthesis of CsA intermediate (30)

★ one isomer has same linker linking through this nitrogen

Scheme 9. Synthesis of CsA-bis-Biotin (31)

★ one isomer has same linker linking through this nitrogen

Dimension® SIRO Standard Curve

STABILIZATION OF SOLID SUPPORT ASSAY REAGENTS

BACKGROUND

The invention relates to solid support reagents that are employed in methods and kits for the determination of analytes in samples, such as patient samples, known or suspected to contain one or more of the analytes.

In the fields of medicine and clinical chemistry, many studies and determinations of physiologically reactive species or analytes are carried out using conjugates involving specific binding pair members and supports and/or labels or the like. Various assay techniques that involve the binding of specific binding pair members are known. The analytes themselves are normally members of specific binding pairs, which allow for their detection employing a corresponding member of the specific binding pair to which the analyte in question belongs.

A variety of clinical conditions may be diagnosed and monitored by detecting the presence of and/or amount of a specific binding pair member analyte in a sample. The results of chemical, biochemical, and biological assays are used to make important decisions; and, therefore, the accuracy and reliability of the result is of utmost importance. Heretofore, control samples of known concentration are assayed periodically, or even simultaneously with the sample to be measured, to calibrate and verify the operation of the assay on the unknown sample. This process reduces, but does not eliminate, the possibility of error in the assay of interest.

As the importance of measuring the presence of an analyte in a sample has increased, a number of means have been developed to detect such analytes. One method involves the conjugation of a label to a specific binding pair member that is employed as an assay reagent to bind to the analyte. In other approaches, a specific binding pair member for the detection of the analyte is conjugated to a support, which is employed as an assay reagent in various ways along with other reagents to detect the analyte in question. Combinations of the above approaches are also utilized.

Assays in which a sample and one or more reagents are reacted in various ways to form a complex such as an antibody/antigen or similar complex, which may then be observed in order to measure the presence or level of an analyte or one or more of several analytes in the sample, are well known. Typically, in some embodiments an antibody is used to assay for the presence and/or amount of a hapten or an antigen for which the antibody is specific. The haptens and antigens include, for example, peptides, proteins, hormones, alkaloids, steroids, antibodies, nucleic acids, and fragments thereof, enzymes, cell surface receptors, and the like.

The usefulness of the assay reagent, however, will depend upon the specificity of the specific binding pair member for the other member, and also will depend upon the level of non-specific binding of the assay reagent or of the components of the assay reagent. The non-specific binding often reduces the sensitivity of the assay. The degree of non-specific binding limits the usefulness of an assay reagent. The greater the non-specific binding in a particular assay reagent, the lesser will be the sensitivity of the determination.

In one approach for reagents involving solid supports, a specific binding pair member such as, for example, an analyte analog, is linked directly to the solid support by covalent binding. Unfortunately, with such reagents, a not insignificant amount of non-specific binding of the specific binding pair member to the surface of the solid support is present. During storage and/or use of such a reagent, non-specifically bound conjugate leaches from the solid support and is present in a liquid assay medium. The presence of such non-specifically bound specific binding pair member leads to inaccuracies in the assay methods employed using the reagent. Non-specific binding refers to non-covalent binding between molecules that is relatively independent of specific surface structures. Non-specific binding may result from several factors including, e.g., hydrophobic interactions between molecules, physical adsorption to the porous surface of solid support, and the like.

There remains a need for assay reagents, which exhibit reduced non-specific binding when used in assays for the detection of one or more analytes. In particular, there remains a need for an assay reagent that comprises a solid support where an analog analyte that may be non-specifically bound to the solid support does not interfere in an assay conducted with such a reagent.

SUMMARY

One embodiment of the present invention is a dry assay reagent, which comprises a solid support and one or more molecules of a receptor immobilized on the solid support. The receptor comprises one or more binding sites for a ligand. A portion of a total number of the binding sites is bound to a conjugate comprising the ligand linked to a specific binding pair member and a portion of the total number of the binding sites is free.

Another embodiment of the present invention is a dry assay reagent, which comprises a particulate solid support and one or more molecules of a biotin-binding partner immobilized on the particulate solid support. A portion of a total number of binding sites of the biotin-binding partner is bound to a conjugate comprising biotin linked to a specific binding pair member and a portion of the total number of the binding sites of the biotin-binding partner is free.

Another embodiment of the present invention is a method for determining the presence and/or amount of an analyte in a sample suspected of containing the analyte. A combination is provided in an aqueous medium the sample and reagents for detecting the analyte wherein at least one of the reagents comprises the dry assay reagent mentioned above. The combination is incubated under conditions for binding of the analyte to one or more of the reagents. The presence and/or amount of binding of the analyte to one or more of the reagents is detected where the presence and/or amount of the binding is related to the presence and/or amount of the analyte in the sample.

BRIEF DESCRIPTION OF THE DRAWINGS

FIG. 7A is a depiction of the structure of a conjugate of antibody for cyclosporin A and biotin.

FIG. 7B is a depiction of the structure of another conjugate of antibody for cyclosporin A and biotin.

FIG. 8 is a depiction of the structure of a conjugate of an antibody for cyclosporin A and chemiluminescent particles.

DETAILED DESCRIPTION OF SPECIFIC EMBODIMENTS

General Discussion

Figure 1:
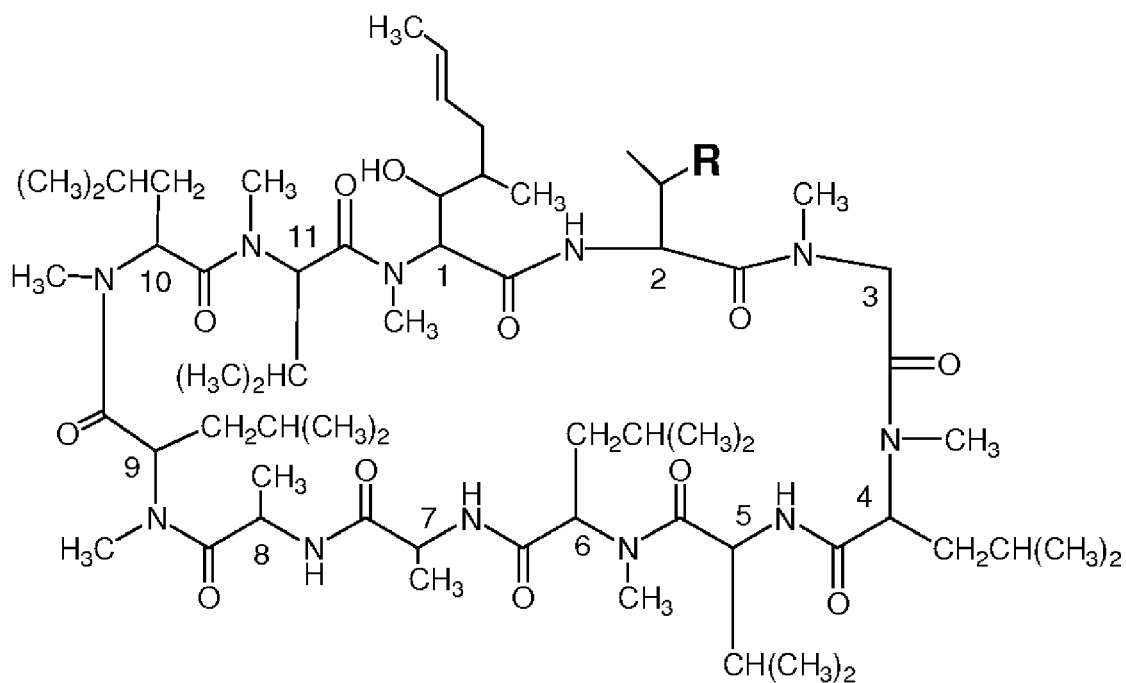
FIG. 1 is a depiction of the structures of cyclosporin A and cyclosporin C.

The reagents and methods of the present invention relate to simple, specific analytical methods for detecting the presence in a sample of one or more analytes. The current methods comprise assay reagents and formats that achieve not only sufficient signal generation but also achieve good sensitivity.

Embodiments of Dry Assay Reagents

Embodiments of the present reagents are dry reagents that are in a form that readily dissolves in an aqueous assay medium. The reagents are stable during formation, in the dry state and when formulated into an assay medium. The dry reagents comprise a specific binding pair (sbp) member that is associated with a solid support. Rather than linked covalently to the solid support, the sbp member is linked covalently to a ligand to form an sbp member-ligand conjugate and the support comprises a receptor for a ligand to which the conjugate is bound. The sbp member is associated with the support by the binding between the ligand and the receptor for the ligand. An excess of binding sites of the receptor is provided on the support so that a portion of the binding sites of the receptor is free. The free binding sites capture sbp member-ligand conjugate that might be non-specifically bound to the solid support and/or that might dissociate from a complex of the conjugate and the receptor on the support during formation of the reagent, during a process for drying the reagent or after the dry reagent dissolves in an aqueous assay medium during an assay. As a result, little or no dissociated or non-specifically bound sbp member-ligand conjugate is available to bind to the binding partner of the sbp member, which is employed as one of the reagents in the assay determination. Thus, the assay sensitivity is enhanced by reduction of non-specifically bound and/or dissociated components of the reagent that might otherwise distort the measurement of the amount of analyte that is to be determined. The reduction of non-specific binding and dissociation is accomplished by a re-equilibration of sbp member-ligand conjugate from binding to the non-specific binding sites on the solid support to binding to the vacant specific binding sites of the receptors on the solid support. As used herein, the term "associated" is to be understood broadly and comprises, for example, a covalent bond or a noncovalent bond, a direct bond and an indirect bond, absorption to a surface and enclosure in a cavity, etc.

In addition, the present invention avoids a problem observed by the present inventors in a process such as, for example, lyophilization, for preparing dry reagents involving immobilized receptor-ligand complexes particularly as regards hydrophobic molecules. The present inventors observed that a certain amount of dissociation of such complexes might occur during the drying process. As mentioned above, in the present reagents an sbp member is linked covalently to a ligand to form an sbp member-ligand conjugate and the support comprises a receptor for a ligand to which the conjugate is bound. The sbp member is associated with the support by the binding between the ligand and the receptor for the ligand. An excess of binding sites of the receptor is provided on the support so that a portion of the binding sites of the receptor is free to capture non-specifically bound and/or dissociated components of the reagent.

As mentioned above, one embodiment of the present invention is a dry assay reagent, which comprises a solid support and one or more molecules of a receptor immobilized on the solid support. The receptor comprises one or more binding sites for a ligand. A portion of a total number of the binding sites is bound to a conjugate comprising the ligand linked, usually covalently, to a specific binding pair member and a portion of the total number of the binding sites is free. A conjugate is a molecule comprised of two or more substructures bound together, either directly or indirectly through a linking group, to form a single structure.

The support may be comprised of an organic or inorganic, solid or fluid, water insoluble material, which may be transparent or partially transparent. The support can have any of a number of shapes, such as particulate including beads and particles, film, membrane, tube, well, strip, rod, planar surfaces such as, e.g., plate, paper-like, etc., fibers, and the like. Depending on the type of assay, the support may or may not be suspendable in the medium in which it is employed. Examples of suspendable supports are polymeric materials such as latex, lipid bilayers or liposomes, oil droplets, cells and hydrogels, magnetic particles, and the like. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

In some embodiments the supports employed are particles. The particles should have an average diameter of at least about 0.02 microns and not more than about 100 microns. In some embodiments, the particles have an average diameter from about 0.05 microns to about 20 microns, or from about 0.3 microns to about 10 microns. In some embodiments the particles have a surface area range of about 10 to about 100 $m^2/g$ and in some embodiments the particles have a surface area in the range of about 10 to about 60 $m^2/g$. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can have a regular or irregular shape. They can be, for example, spheres, spheroids or spheres possessing cavities or pores of greater or lesser size. The particles can comprise several layers, such as what are termed core and shell particles, having a core and one or more enveloping layers. The particles can be biological materials such as cells and microorganisms, e.g., erythrocytes, leukocytes, lymphocytes, hybridomas, *streptococcus, Staphylo-* coccus aureus, E. coli, viruses, and the like. The particles can also be particles comprised of organic and inorganic polymers, liposomes, latex particles, magnetic or non-magnetic particles, phospholipid vesicles, chylomicrons, lipoproteins, dye crystals, metal sols, silica particles, glass particles, magnetic particles, oil drops, lipid particles, dextran and protein aggregates and the like.

In some embodiments the particles are microparticles, which are particles that have an approximate diameter of at least 20 nm and not more than 20 microns, or between 40 nm and 10 microns, or between 0.1 and 10 microns, or between 0.1 and 5 microns, or between 0.15 and 2 microns. In many embodiments the microparticles are particles that can be suspended in aqueous solutions.

Polymer particles can be formed of addition or condensation polymers. The particles will be readily dispersible in an aqueous medium and can be adsorptive or functionalizable so as to permit conjugation to an sbp member, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

In some embodiments, the particles are magnetic particles. When the particles are magnetic, the magnetic material contained in the particles may be any magnetic material susceptible to attraction by a permanent magnet or an electromagnet. Examples of such magnetic materials include magnetic iron oxides, magnetic chromium dioxides ($CrO_2$), $MnFeO_4$, $ZnFeO_4$, $CoFe_2O_4$ and similar magnetic materials.

A particular example of embodiments of magnetic particles include those that have a magnetic core surrounded by a polymeric material. The polymeric material may be any polymeric material suitable for use in assays such as, e.g., immunoassays; polystyrene and polystyrene-divinyl benzene are preferred for their easy availability. Further, the polymeric material preferably either has functional groups reactive with aldehyde groups or can be modified by methods known in the art to contain such aldehyde-reactive groups. Examples of such functional groups include amine, hydrazine, hydrazide, aminooxy, cyanide, alcohol groups, and the like.

Another example of magnetic particles which may be used in practicing the invention are chromium dioxide magnetic particles (chrome particles) having pendent surface groups which are aldehyde-reactive or which can be modified to contain such aldehyde-reactive groups. Such magnetic chromium oxide particles include those comprising a core of $CrO_2$ that has a reduced surface, which is then coated with silica and further coated with a silane as taught in U.S. Pat. No. 4,661,408, the relevant disclosure of which is incorporated herein by reference. The outer silane layer is capable of binding proteins including antibodies and antigen species, ligands, haptens or linking compounds directly or through intermediate coupling agents to the coated core. Linking and/or coupling agents useful in linking components include dicarboxylic acids and anhydrides, polyamines, polyaldehydes, and heterobifunctional agents such as 2-iminothiolane hydrochloride, sulfosuccinimidyl-4-(N-maleimidomethyl)cyclohexane-1-carboxylate, m-maleimidosuccin-imide ester, N-succinimidyl-(4-iodoacetyl)aminobenzoate, and similar species known to those skilled in the art. Other particular embodiments of magnetic and non-magnetic particles that may be employed in the present reagents are those disclosed in U.S. Pat. No. 6,231,982, the relevant disclosure of which is incorporated herein by reference.

One or more molecules of a receptor are immobilized on the solid support. The receptor comprises one or more binding sites for a ligand. The terms ligand and receptor are used herein to designate molecules that are involved in the binding of a ligand-sbp member conjugate to a receptor that is associated with a solid support. Ligands and receptors are sbp members but are distinguished herein for purposes of describing the present methods and reagents. The term sbp member is used herein to denote a reagent that is involved in the detection of an analyte rather than in the binding of a moiety to the solid support, for which the terms ligand and receptor are used. A receptor is any molecule capable of recognizing a particular spatial and polar organization of another molecule, e.g., epitopic or determinant site. Generally, the molecules have areas on their surfaces or in cavities giving rise to specific recognition between the two molecules. The recognition site on the receptor that specifically binds to a site on the ligand is referred to herein as a binding site. The term specific binding as used herein is the specific recognition of one of two different molecules for the other compared to substantially less recognition of other molecules. A ligand is any organic compound for which a receptor naturally exists or can be prepared. Examples of receptors that may be employed in the present reagents include biotin-binding partners, e.g., streptavidin and avidin, antibodies, single stranded antisense nucleic acids, aptamers, hormone receptors, enzymes, and so forth.

A single molecule of receptor can have one or more binding sites for a ligand. The number of binding sites of the receptor for the ligand may be 1, or 2, or 3, or 4, or 5, or 6, or 7 and so forth wherein the range is 1 to about 8, or 1 to about 7, or 1 to about 6, or 1 to about 5, or 1 to about 4, or 1 to about 3, or 1 to 2, or 2 to about 7, or 2 to about 6, or 2 to about 5, or 2 to about 4, or 2 to about 3, or 3 to about 7, or 3 to about 6, or 3 to about 5, or 3 to about 4, and so forth.

In many embodiments the ligand of the ligand-sbp member conjugate is a small molecule or residue of a small molecule. Small molecules have a molecular weight of from about 100 to about 2000, or about 150 to about 1000, and a receptor for the small molecule either exists or can be prepared. Examples of small molecules include biotin and derivatives of biotin such as, for example, bis-biotin and so forth, lysergic acid, fluorescein and fluorescein derivatives, dinitrophenol, digoxigenin, single stranded nucleic acids, vitamin $B_{12}$, enzyme suicidal inhibitors, and the like. The corresponding receptors for the aforementioned small molecules are, respectively, a biotin-binding partner, e.g., avidin or streptavidin, anti-lysergic acid, anti-fluorescein, anti-dinitrophenol, anti-digoxigenin, single stranded anti-sense nucleic acids, intrinsic factor, and enzymes.

As mentioned above, in addition to ligand-receptor interactions, the present reagents and methods also involve sbp members as distinguished from the ligand and receptor molecules discussed above. A member of a specific binding pair ("sbp" member) is one of two different molecules having an area on the surface or in a cavity that specifically binds to and is therefore defined as complementary with a particular spatial and polar organization of the other molecule. Complementary sbp members bind to one another. With respect to two complementary sbp members, one may be referred to as the "binding partner" for the other. Examples of sbp members include antibody-antigen interactions, enzyme-substrate interactions, polynucleotide interactions, and so forth. Illustrative sbp members include naturally occurring receptors, e.g., thyroxine binding globulin, antibodies, enzymes, Fab fragments, lectins, nucleic acids, protein A, complement component Clq, and the like. At least one of the sbp members of the present reagents and methods is one that binds specifically to an analyte such as, for example, an antibody for the analyte, or one that binds to an sbp member specific for the analyte such as an analyte analog and, thus, can compete with the analyte for binding to the sbp member specific for the analyte, which may be, for example, an antibody for the analyte.

Small molecules, in particular, and ligands, in general, can be bound to an sbp member to form a ligand-sbp member conjugate having at least one, or 2 to about 20, small molecules per sbp member depending on the nature of the sbp member. Larger sbp members such as, e.g., antibodies, have 1 to about 20 small molecules bound thereto. Bonding of the small molecule to the sbp member may be accomplished by covalent binding, which usually involves chemical reactions that result in replacing a hydrogen atom of the small molecule with a bond to the sbp member, or by a linking group between the small molecule and the sbp member of any size but preferably no larger than necessary to permit binding to the conjugate of both a receptor for the small molecule and the sbp member.

In some embodiments, the linking group may comprise about 2 to about 50 atoms, or 4 to about 30 atoms, not counting hydrogen and may comprise a chain of from 2 to about 30 atoms, or 3 to about 20 atoms, each independently selected from the group normally consisting of carbon, oxygen, sulfur, nitrogen, and phosphorous. Part or all of the linking group may be a portion of the molecule being linked to another molecule such as, for example, an amino acid residue on a poly(amino acid) and the like.

The number of heteroatoms in the linking groups will normally range from about 0 to about 20, or 1 to about 15, or about 2 to about 10. The linking groups may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. One specific embodiment of a linking group comprising heteroatoms is an oxime functionality as mentioned above.

For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or $\alpha$-, $\beta$-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed. Various linking groups are well known in the art; see, for example, Cautrecasas, *J. Biol. Chem.* (1970) 245:3059.

As mentioned above, a portion of a total number of the binding sites of the receptor is bound to a conjugate comprising the ligand covalently linked, either directly or through a linking group, to an sbp member and a portion of the total number of the binding sites of the receptor is free. The number of free binding sites, i.e., the number of binding sites of the receptor that are free for binding to ligand is sufficient to capture all molecules of conjugate that may be non-specifically bound to the solid support and/or that may dissociate from the solid support. The molar ratio of the total number of binding sites of the receptor to the number of molecules of ligand of the ligand-sbp member conjugate is dependent on the nature of the receptor, the nature of the ligand, and the like. In many embodiments the molar ratio of the total number of binding sites of the receptor to the number of molecules of ligand of the ligand-sbp member conjugate is greater than 1. The molar ratio of the total number of binding sites of the receptor to the number of molecules of ligand is about 1.2 to about 10, or about 1.3 to about 9, or about 1.4 to about 8, or about 1.5 to about 7, or about 1.5 to about 6, or about 1.5 to about 5, or about 1.5 to about 4, or about 1.6 to about 6, or about 1.6 to about 5, or about 1.6 to about 4, or about 1.7 to about 6, or about 1.7 to about 5, or about 1.7 to about 4, or about 1.8 to about 6, or about 1.8 to about 5, or about 1.8 to about 4, or about 1.9 to about 6, or about 1.9 to about 5, or about 1.9 to about 4, and so forth. As mentioned above, a particular receptor may have one binding site for the ligand per molecule or it may have more than one binding site for the ligand per molecule of receptor.

The total number of binding sites referred to above is the total number of binding sites for all molecules of the receptor that are present on the solid surface. For example, streptavidin has four binding sites for biotin. Thus, the total number of binding sites for streptavidin on a solid support is the total number of molecules of streptavidin on the solid support times the number of binding sites for each molecule of streptavidin, namely, four. In this particular example where streptavidin-biotin binding is involved, a desirable embodiment of the present reagent has one molecule of streptavidin per two molecules of biotin so that the molar ratio of the total number of binding sites to molecules of biotin is 4:2 or 2:1. Such a ratio, it has been discovered, stabilizes the streptavidin tetrameric structure while allowing for capture of non-specifically bound and/or dissociated conjugate by the remaining binding sites of the streptavidin tetramer.

The reactions involved in the preparation of the assay reagent discussed above usually are carried out in a liquid medium. Following preparation of the assay reagent in a liquid medium, the resulting product is dried by conventional techniques, which include, for example, lyophilization, application of heat, application of a vacuum, desiccation, moisture absorption, solvent vaporization, and the like, or a combination of the above techniques. Depending on the nature of the solid support of the present reagents, the dry reagent may be prepared in the form of a tablet, powder, and the like. For a support such as paper, microtiter plate, chips, and the like, the surface of the support may comprise, in a dry form, molecules of receptor with binding sites that are free and binding sites that are bound to ligand-sbp member conjugate. The dry reagent is stored at about 0° C. to about 35° C., or about 2° C. to about 30° C., or about 5° C. to about 25° C., or at ambient or room temperature, or in some embodiments below 0° C., until it is used in an assay method for the determination of an analyte. The assay reagent is prepared and dried in a manner that renders the resulting dry reagent readily able to be reconstituted in an assay medium, which is usually an aqueous medium. The dry assay reagent may contain one or more substances or excipients that promote the reconstitution of the dry reagent in an assay medium. Such substances include, for example, trehalose, polyethylene glycol 8000 and the like.

Methods Employing the Present Dry Assay Reagents

As mentioned above, the present dry assay reagents may be employed in methods for determining the presence and/or amount of an analyte in a sample suspected of containing the analyte. The assay methods employed measure the amount of analyte in the sample and may be quantitative, semiquantitative, or qualitative. For example, a method, which merely detects the presence or absence of an analyte in a sample suspected of containing the analyte, is considered to be included within the scope of the present invention. The terms "detecting" and "determining," as well as other common synonyms for measuring, are contemplated within the scope of the present invention.

The sample and reagents for detecting the analyte are combined in an aqueous medium. At least one of the reagents comprises the dry assay reagent described above. Other reagents employed depend on the nature of the analyte, the nature of the particular assay method, the nature of the signal molecule, the nature of the detection system and the like, examples of which are discussed below. The combination is incubated under conditions for binding of the analyte to one or more of the reagents. The presence and/or amount of binding of the analyte to one or more of the reagents is detected where the presence and/or amount of the binding is related to the presence and/or amount of the analyte in the sample.

The analyte is a compound or composition to be detected. The analyte can be comprised of a member of a specific binding pair (sbp) where the complementary member of the specific binding pair is used in the detection of the analyte. Monoepitopic ligand analytes will generally be from about 100 to 2,000 molecular weight, more usually from 125 to 1,000 molecular weight. The analytes include drugs, metabolites, pesticides, pollutants, and the like. Representative analytes, by way of example and not limitation, include (i) alkaloids such as morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g., Phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which include ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which include cannabinol and tetrahydrocannabinol; (viii) hormones such as thyroxine (T4), triiodothyronine (T3), cortisol, triiodothyronine, testosterone, estradiol, estrone, progesterone, polypeptides such as angiotensin, LHRH, and immunosuppressants such as cyclosporin (A, B, C, D, E, F, G, etc.), FK506, mycophenolic acid (MPA), and so forth; (ix) vitamins such as A, B, e.g. B12, C, D, E and K, folic acid, thiamine; (x) prostaglandins, which differ by the degree and sites of hydroxylation and unsaturation; (xi) tricyclic antidepressants, which include imipramine, dismethylimipramine, amitriptyline, nortriptyline, protriptyline, trimipramine, chlomipramine, doxepine, and desmethyldoxepin; (xii) antineoplastics, which include methotrexate; (xiii) antibiotics, which include penicillin, chloromycetin, actinomycetin, tetracycline, terramycin, the metabolites and derivatives; (xiv) nucleosides and nucleotides, which include ATP, NAD, FMN, adenosine, guanosine, thymidine, and cytidine with their appropriate sugar and phosphate substituents; (xv) miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; (xvi) metabolites related to diseased states include spermine, galactose, phenylpyruvic acid, and porphyrin Type 1; (xvii) aminoglycosides, such as gentamicin, kanamicin, tobramycin, and amikacin; and (xviii) pesticides such as polyhalogenated biphenyls, phosphate esters, thiophosphates, carbamates, polyhalogenated sulfenamides, their metabolites and derivatives.

Polyvalent analytes are normally poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The analyte includes a wide variety of proteins that may be of a family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides. The term analyte further includes oligonucleotide and polynucleotide analytes such as m-RNA, r-RNA, t-RNA, DNA, DNA-RNA duplexes, etc.

The sample to be analyzed is one that is suspected of containing the analyte. The analyte may be a molecule found directly in a sample such as biological tissue, including body fluids, from a host. The samples are preferably from humans or animals and include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum and, in a particular embodiment the sample is whole blood.

The sample can be prepared in any convenient medium. Conveniently, the sample may be prepared in an assay medium, which is discussed more fully below. In some instances a pretreatment may be applied to the sample such as, for example, to lyse blood cells, and the like. The sample can be examined directly or may be pretreated to render the analyte more readily detectable by removing unwanted materials. The sample may be pretreated to separate or lyse cells; precipitate, hydrolyse or denature proteins; hydrolyze lipids; solubilize the analyte; or the like. Such pretreatments may include, without limitation: centrifugation; treatment of the sample with an organic solvent, for example, an alcohol, such as methanol; and treatment with detergents. Such pretreatment is usually performed in a medium that does not interfere subsequently with an assay.

The sample can be prepared in any convenient medium that does not interfere with an assay. An aqueous medium is preferred and typically is one that may be solely water or may include from 0.1 to about 40 volume percent of a cosolvent such as, for example, an organic solvent, which may be an alcohol, ether, ester, amide and the like. Various ancillary materials may be employed in an assay. The medium may comprise one or more preservatives as are known in the art such as, for example, sodium azide, neomycin sulfate, PROCLIN® 300, Streptomycin, and the like. In addition, stabilizers for the assay medium and the assay components may be present in the assay medium. Frequently, in addition to these additives, proteins may be included, such as albumins. Other ancillary materials include, for example, quaternary ammonium salts, polyanions such as dextran sulfate, surfactants, particularly non-ionic surfactants, binding enhancers, e.g., polyalkylene glycols, and the like.

The pH for the medium will usually be in the range of about 4 to about 11, more usually in the range of about 5 to about 10, and preferably in the range of about 6.5 to about 9.5. Various buffers may be used to achieve the desired pH and maintain the pH during the incubation period. Illustrative buffers include borate, phosphate, carbonate, tris, barbital, PIPES, HEPES, MES, ACES, MOPS, BICINE, and the like. The medium may also comprise agents for preventing the formation of blood clots. Such agents are well known in the art and include, for example, EDTA, EGTA, citrate, heparin, and the like.

In the assay methods discussed herein, a signal producing system ("sps") is employed for the detection of an analyte. The sps comprises one or more components, at least one component being a detectable label, which generate a detectable signal that relates to the amount of bound and/or unbound label, i.e. the amount of label bound or not bound to the compound being detected, i.e., the analyte. The label is any molecule that produces or can be induced to produce a signal, and may be, for example, a fluorescer, radiolabel, enzyme, chemiluminescer or photosensitizer. Thus, the signal is detected and/or measured by detecting enzyme activity, luminescence, light absorbance or radioactivity as the case may be.

Suitable labels include, by way of illustration and not limitation, enzymes such as alkaline phosphatase, β-galactosidase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}$I, $^{131}$I, $^{14}$C, $^{3}$H, $^{57}$Co and $^{75}$Se; particles such as latex or carbon particles; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; the relevant disclosures of which are incorporated herein by reference.

There are numerous methods by which the label can produce a signal detectable by external means, desirably by visual examination, for example, by electromagnetic radiation, heat, and chemical reagents. The label or other sps members can also be associated with an sbp member, another molecule or to a support. Labels include groups detectable by means of electromagnetic radiation or by electrochemical detection including dyes, fluorescers, chemiluminescers, and radioactive isotopes.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in U.S. Pat. No. 5,185,243, columns 11-13, incorporated herein by reference.

The label and/or other sps member may be associated with an sbp member, a support, another molecule and so forth. For example, the label can be bound covalently to an sbp member such as, for example, an antibody; a receptor for an antibody, a receptor that is capable of binding to a small molecule conjugated to an antibody, or a ligand analog. Bonding of the label to the sbp member may be accomplished by chemical reactions as discussed above, which may involve direct bonding or bonding through a linking group between the label and the sbp member or the like. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art and include those discussed above. Furthermore, see, for example, U.S. Pat. No. 3,817,837, the relevant disclosure of which is incorporated herein by reference.

In some embodiments, the sps has at least first and second sps members. The designation "first" and "second" is completely arbitrary and is not meant to suggest any order or ranking among the sps members or any order of addition of the sps members in the present methods. In this system, the sps members are related in that activation of one member of the sps produces a product such as, e.g., light, which results in activation of another member of the sps. The second sps member usually generates a detectable signal that relates to the amount of analyte in the sample.

In some embodiments the first sps member is a sensitizer, such as, for example, a photosensitizer and the second sps member is a chemiluminescent composition that is activated as a result of the activation of the first sps member. The sensitizer may be any moiety that upon activation produces a product that activates the chemiluminescent composition, which in turn generates a detectable signal. In many embodiments the sensitizer is capable of generating singlet oxygen upon activation. Examples of photosensitizers and chemiluminescent compositions that may be utilized are those set forth in U.S. Pat. Nos. 5,340,716 and 6,153,442, the disclosures of which are incorporated herein by reference.

For immunoassays, the methods employ at least one antibody for the analyte. By the phrase "antibody for the analyte" is meant an antibody that binds specifically to the analyte and/or analyte analog and does not bind to any significant degree to other assay components or components of the sample such that the analysis for the analyte would be distorted. An analyte analog is a modified analyte that can compete with the analyte for a receptor, the modification providing means to join an analyte analog to another molecule. The analyte analog will usually differ from the analyte by more than replacement of a hydrogen with a bond which links the analyte analog to a hub or label, but need not. The analyte analog binds to the receptor in a manner similar to the binding of analyte to the receptor. The analyte analog may be, for example, the analyte conjugated to another molecule through a linking group, an antibody directed against the idiotype of an antibody to the analyte, and so forth.

Antibodies specific for an analyte for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1-24 (1975); Broughton and Strong, Clin. Chem. 22: 726-732 (1976); and Playfair, et al., Br. Med. Bull. 30: 24-31 (1974).

Antibodies can also be obtained by somatic cell hybridization techniques, such antibodies being commonly referred to as monoclonal antibodies. Monoclonal antibodies may be produced according to the standard techniques of Köhler and Milstein, Nature 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, the reagents can be combined sequentially. When various agents are combined other than concomitantly (simultaneously), one or more may be combined with one or more of the remaining agents to form a subcombination. The dry assay reagent of the present embodiments may be added directly to the assay medium or it may be reconstituted in an appropriate medium prior to addition to the assay medium.

One or more incubation periods may be applied to the assay medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures range from about 5° to about 99° C., or from about 15° C. to about 70° C., or from 20° C. to about 45° C. The time period for the incubation is about 0.2 seconds to about 24 hours, or about 1 second to about 6 hours, or about 2 seconds to about 1 hour, or about 1 to about 15 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., or from about 15 to about 40° C.

The concentration of analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents.

The concentrations of the various reagents in the assay medium will generally be determined by the concentration range of interest of the analyte, the nature of the assay, and the like. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of the analytes normally determine the concentrations of the various reagents.

Following any incubation periods for binding of the respective reagents, an examination of the medium or the support is carried out. In many embodiments the examination of the medium involves detection of a signal from the medium or from the solid support. The presence and/or amount of the signal is related to the presence and/or amount of the analyte in the sample. The particular mode of detection depends on the nature of the sps. As discussed above, there are numerous methods by which a label of an sps can produce a signal detectable by external means, desirably by visual examination, and include, for example, electromagnetic radiation, electrochemistry, heat, radioactivity detection, chemical reagents and so forth.

Activation of a signal producing system depends on the nature of the signal producing system members. For an sps member that is a sensitizer that is activated by light, the sps member is irradiated with light. Other activation methods will be suggested to those skilled in the art in view of the disclosures herein.

The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the analyte present in a sample. Temperatures during measurements generally range from about 10° to about 70° C., or from about 20° to about 45° C., or about 20° to about 25° C. In one approach standard curves are formed using known concentrations of the analytes to be screened. As discussed above, calibrators and other controls may also be used.

Examples of Assays Employing Embodiments of the Dry Assay Reagent

As mentioned above, the dry assay reagents discussed above can be utilized in binding assays for analytes. The dry assay reagents have application to all of the assays discussed below as well as to other assays involving support reagents not specifically mentioned herein. The assay methods usually involve a sample suspected of containing an analyte, which is combined in an assay medium with reagents for carrying out the assay. Such reagents include a support or solid phase reagent. Other assay reagents can include a binding partner for the analyte if the sbp member on the solid support is not a binding partner for the analyte, analyte analogs, other solid supports to which one of the reagents is bound, binding partners for sbp members, and so forth. One or more of the reagents may be part of a signal producing system where at least one of the reagents can be labeled. The reagents are chosen such that a signal is obtained from a label in relation to the presence or amount of analyte in the sample. The assay can be performed either without separation (homogeneous) or with separation (heterogeneous) of any of the assay compounds or products. Since solid supports are utilized, the assay is usually heterogeneous although homogeneous formats using such reagents are known.

Heterogeneous assays usually involve one or more separation steps and can be competitive or non-competitive. A variety of competitive and non-competitive heterogeneous assay formats are disclosed in U.S. Pat. No. 5,089,390, column 14, line 25 to column 15, line 9, which is incorporated herein by reference. In a typical competitive heterogeneous assay, a support having an antibody for analyte bound thereto is contacted with a medium containing the sample and analyte analog conjugated to a detectable label such as an enzyme (the "conjugate"). Analyte in the sample competes with the conjugate for binding to the antibody. After separating the support and the medium, the label activity of the support or the medium is determined by conventional techniques and is related to the amount of analyte in the sample. The dry assay reagent in accordance with the present embodiments may be employed as the support reagent referred to above. In this instance, the support has a receptor such as, e.g., streptavidin, bound to it and a ligand-antibody, e.g., biotin-antibody, conjugate is bound to the support by the binding of the streptavidin on the support and the biotin of the conjugate.

A typical non-competitive sandwich assay is an assay disclosed in U.S. Pat. No. 4,486,530, column 8, line 6 to column 15, line 63, which is incorporated herein by reference. In this method, an immune sandwich complex is formed in an assay medium. The complex comprises the analyte, a first antibody (monoclonal or polyclonal) that binds to the analyte and a second antibody that binds to the analyte or a complex of the analyte and the first antibody. Subsequently, the immune sandwich complex is detected and is related to the amount of analyte in the sample. The immune sandwich complex is detected by virtue of the presence in the complex of a label wherein either or both the first antibody and the second antibody contain labels or substituents capable of combining with labels. In this instance, the dry assay reagent in accordance with the present disclosure comprises a support to which a receptor, e.g., streptavidin, is bound and a ligand-antibody, e.g., biotin-antibody, conjugate is bound to the support by the binding of the streptavidin on the support and the biotin of the conjugate. The antibody is one of the aforementioned first or second antibodies.

Sandwich assays find use for the most part in the detection of antigen and antibody analytes. In the assay the analyte is bound by two antibodies specific for the analyte and, thus, the assay is also referred to as the two-site immunometric assay. In one approach a first incubation of unlabeled antibody coupled to a support, otherwise known as the insolubilized antibody, is contacted with a medium containing a sample suspected of containing the analyte. After a wash and separation step, the support is contacted with a medium containing the second antibody, which generally contains a label, for a second incubation period. The support is again washed and separated from the medium and either the medium or the support is examined for the presence of label. The presence and amount of label is related to the presence or amount of the analyte. For a more detailed discussion of this approach see U.S. Pat. Nos. Re 29,169 and 4,474,878, the relevant disclosures of which are incorporated herein by reference. In this instance, the dry assay reagent in accordance with the present disclosure comprises a support to which a receptor, e.g., streptavidin, is bound and a ligand-antibody, e.g., biotin-antibody, conjugate is bound to the support by the binding of the streptavidin on the support and the biotin of the conjugate. The antibody is the unlabeled antibody referred to above.

In a variation of the above sandwich assay the sample in a suitable medium is contacted with labeled antibody for the analyte and incubated for a period of time. Then, the medium is contacted with a support to which is bound a second antibody for the analyte. After an incubation period, the support is separated from the medium and washed to remove unbound reagents. The support or the medium is examined for the presence of the label, which is related to the presence or amount of analyte. For a more detailed discussion of this approach see U.S. Pat. No. 4,098,876, the relevant disclosure of which is incorporated herein by reference. In this instance, the dry assay reagent in accordance with the present disclosure comprises a support to which a receptor, e.g., streptavidin, is bound and a ligand-antibody, e.g., biotin-antibody, conjugate is bound to the support by the binding of the streptavidin on the support and the biotin of the conjugate. The antibody is the second antibody for the analyte referred to above.

In another variation of the above, the sample, the first antibody bound to a support and the labeled antibody are combined in a medium and incubated in a single incubation step. Separation, wash steps and examination for label are as described above. For a more detailed discussion of this approach see U.S. Pat. No. 4,244,940, the relevant disclosure of which is incorporated herein by reference. In this instance, the dry assay reagent in accordance with the present disclosure comprises a support to which a receptor, e.g., streptavidin, is bound and a ligand-antibody, e.g., biotin-antibody, conjugate is bound to the support by the binding of the streptavidin on the support and the biotin of the conjugate. The antibody is the first antibody referred to above.

Another specific example of an embodiment of an assay format in which the present dry assay reagent may be employed is ACMIA (Affinity Chromium dioxide Mediated Immuno Assay) (see, for example, U.S. Pat. No. 7,186,518, the relevant disclosure of which is incorporated herein by reference). For the ACMIA assay format, the dry assay reagent in accordance with the disclosure herein comprises chrome particles to which a receptor, e.g., streptavidin, is bound. A ligand, e.g., biotin, conjugate comprising biotin linked to an analyte or analyte analog is bound to the streptavidin. The molar ratio of number of binding sites of the molecules of streptavidin to the biotin is greater than 1. The reagents also include an antibody for the analyte. This antibody is crosslinked to a reporter enzyme (e.g., beta-galactosidase) and is added to a reaction vessel in excess. The antibody-enzyme conjugate is mixed with a sample to allow the analyte to bind to the antibody. Next, the dry chrome reagent mentioned above is added to bind up any excess antibody-enzyme conjugate. Then, a magnet is applied, which pulls all of the chrome and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the presence of amount of rapamycin in the sample.

In another specific example of a sandwich assay format, the dry assay reagent comprises chrome particles to which a receptor, e.g., streptavidin, is bound. A ligand, e.g., biotin, conjugate comprising biotin linked to an antibody for the analyte is bound to the streptavidin. The molar ratio of number of binding sites of the molecules of streptavidin to the biotin is greater than 1. A second antibody (or binding protein) specific for the analyte is conjugated to a reporter enzyme is employed. In this format, the dry assay reagent is added to an assay medium along with the sample. The medium is incubated so that all of the analyte in the sample becomes bound to the chrome particles. The chrome particles are washed, using a magnet to separate the bound analyte from the supernatant. Then, the second antibody conjugated to the beta-galactosidase is added and the medium is incubated such that a sandwich is formed comprising the analyte, the chrome particle and the second antibody. After washing, the amount of enzyme that is bound to the chrome particles is measured and is related to the presence and/or amount of the analyte in the sample.

Another specific example of an assay format in which the present dry assay reagent may be employed is an induced luminescence assay as described is U.S. Pat. No. 5,340,716, the relevant disclosure thereof is incorporated herein by reference. In one approach the assay uses a particle incorporating a photosensitizer and a label particle incorporating a chemiluminescent compound. The label particle is conjugated to an sbp member that is capable of binding to an analyte to form a complex, or to a second sbp member to form a complex, in relation to the presence of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of analyte present. In this instance, the dry assay reagent in accordance with the present disclosure comprises a label particle to which a receptor, e.g., streptavidin, is bound and a ligand-antibody, e.g., biotin-antibody, conjugate is bound to the support by the binding of the streptavidin on the support and the biotin of the conjugate. The sbp member is that referred to above that is capable of binding to the analyte.

General Description of Preparation of Compounds

The EPRM chemibead is prepared in a manner similar to the method described in U.S. Pat. No. 6,153,442, the relevant disclosure of which is incorporated herein by reference. The EPRM chemibead comprises an aminodextran inner layer and a dexal outer layer having free aldehyde functionalities. Dexal is dextran aldehyde; see, for example, U.S. Pat. Nos. 5,929,049 and 7,172,906. The reaction is carried out at a temperature of about 0 to about 40° C., for a period of about 16 to about 64 hours at a pH of about 5.5 to about 7.0, or about 6, in a buffered aqueous medium employing a suitable buffer such as, for example, MES or the like. The reaction is quenched by addition of a suitable quenching agent such as, for example, carboxymethoxyoxime (CMO), or the like and subsequent washing of the particles.

The APRM chemibead is a polystyrene bead with chelated europium and thioxene as the chemiluminescent composition. The APRM chemibead is prepared in a manner similar to the method described in U.S. Pat. No. 6,153,442, the relevant disclosure of which is incorporated herein by reference. The APRM chemibead comprises an aminodextran layer having free amine functionalities.

Figure 10:
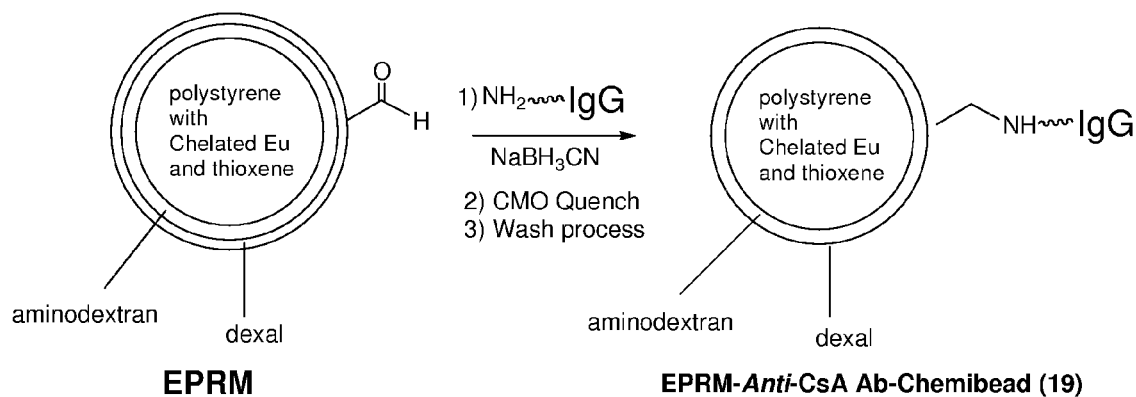
FIG. 10 is a depiction of the preparation of a conjugate of an antibody for cyclosporin A and a chemiluminescent particle.

Preparation of CsA antibody-chemiluminescent particle reagent. The preparation of conjugates of CsA antibody and particles may be accomplished according to the following embodiments. For example, EPRM-anti-CsA-antibody-chemibead (19) is prepared in buffer (for example, MES, pH=6.0, neowater (83%) and MES buffer (50 mM), or the like) with reductive amination of free amine groups of the antibody with aldehyde groups of the EPRM chemibead in the presence of NaBH$_3$CN (FIG. 10, Scheme 6) under reductive amination conditions as discussed above. Any remaining aldehyde groups from ERPM are quenched as described above and the resulting particles are washed as discussed above.

Figure 11:
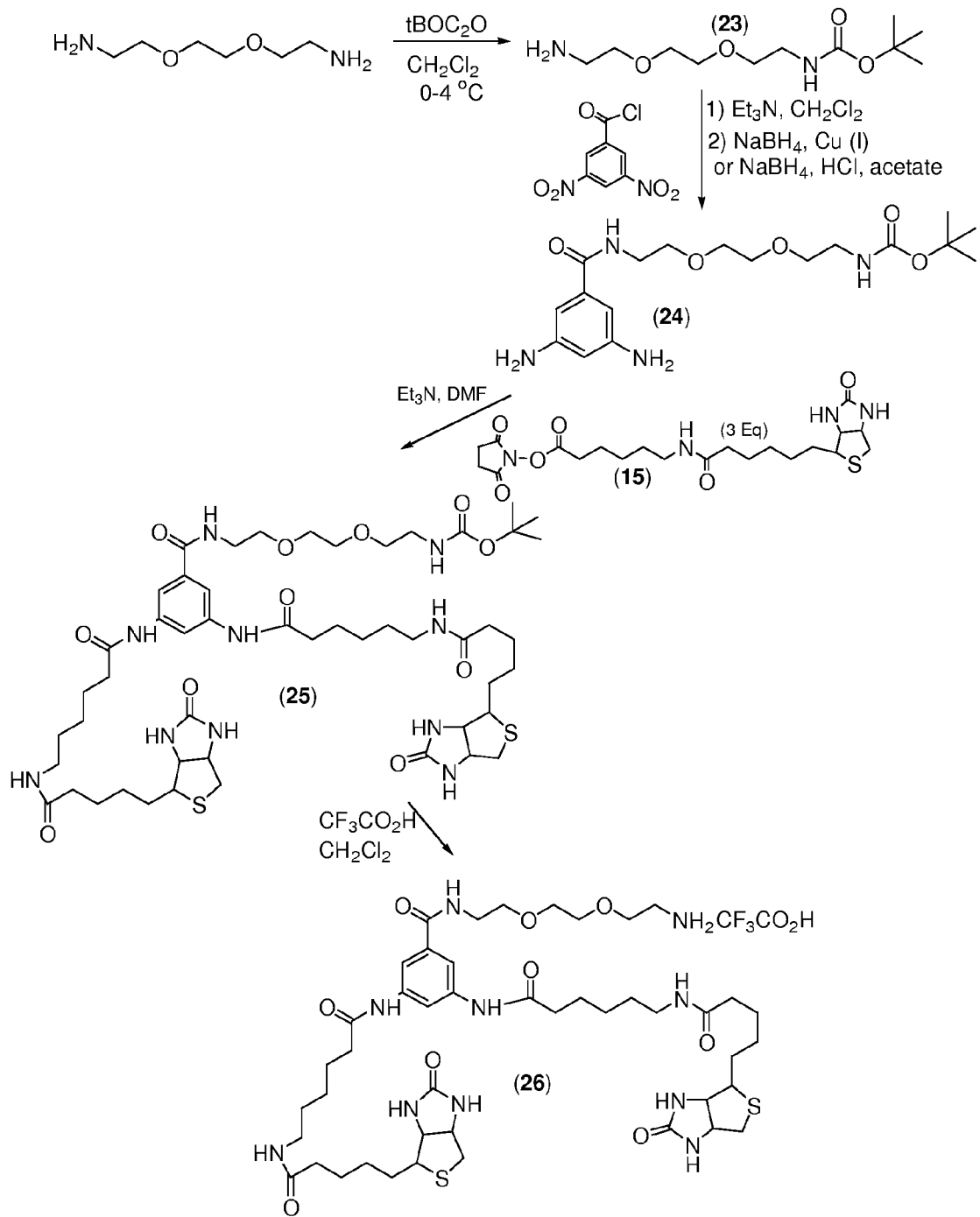
FIG. 11 is a depiction of the preparation of bis-biotin having a linking group.

Preparation of CsA-bis-biotin conjugates. In some embodiments, a CsA-bis-biotin (31) may be prepared by way of illustration and not limitation. The preparation of CsA-bis-biotin (31) may be achieved, for example, using two coupling partners, bis-biotin linker (26) and CsA-derivative (30) (FIGS. 20-22, Schemes 11-13). A synthetic pathway for preparation of 26 is carried out in a total of five-steps. (A preparation of compound (26) is described in U.S. Pat. No. 6,153,442, the relevant disclosure of which is incorporated herein by reference. However, the previous synthesis of 26 required ten reaction steps. The synthetic approach disclosed herein is more efficient and cost-effective than the previous synthesis.) In the present embodiments the synthesis of 26 commences with selective protection of one amine in DA-10 with a suitable protection agent such as, for example, t-butyl anhydride, or the like to give compound (23) (FIG. 11, Scheme 7). The reaction is carried out in an organic solvent such as, for example, methylene chloride, DMF, or the like, at a temperature of about 0° C. to about 5° C., for a period of about 1 to about 24 hours at a pH of about 7.5 to about 13. Acylation of 23 with N-benzyloxycarbonyl-5-aminopentanoic anhydride under basic conditions. The reaction is carried out at a temperature of about 0 to about 80° C., for a period of about 3 to about 16 hours under basic conditions at a pH of about 7.5 to about 11 such as, for example, in the presence of triethyl amine ($Et_3N$), diisopropyl ethyl amine, and the like in an organic solvent such as, for example, methylene chloride, acetonitrile (AcCN), DMF, THF, diethyl ether and the like. Reduction of the nitro groups to amine is carried out using a suitable reducing agent such as, for example, $NaBH_4$, or Cu (I) acetyl acetone or $NaBH_4$, HCl or 10% Pd on carbon, or the like, gives diamine compound (24). Reaction conditions are chosen that are appropriate for the particular reducing agent employed. Reaction of diamine (24) with a commercially available linker, for example, sulfo-NHS-LC-Biotin, NHS-$PEO_4$-biotin or the like gives compound (25). Selective deprotecting of the t-Boc protecting group of 25 under acidic conditions such as, for example, trifluoroacetic acid, a mineral acid, e.g., HCl, etc., or the like in an organic solvent such as, for example, methylene chloride, DMF, or the like gives the desired bis-biotin linker (26) (FIG. 11, Scheme 7).

Figure 12:
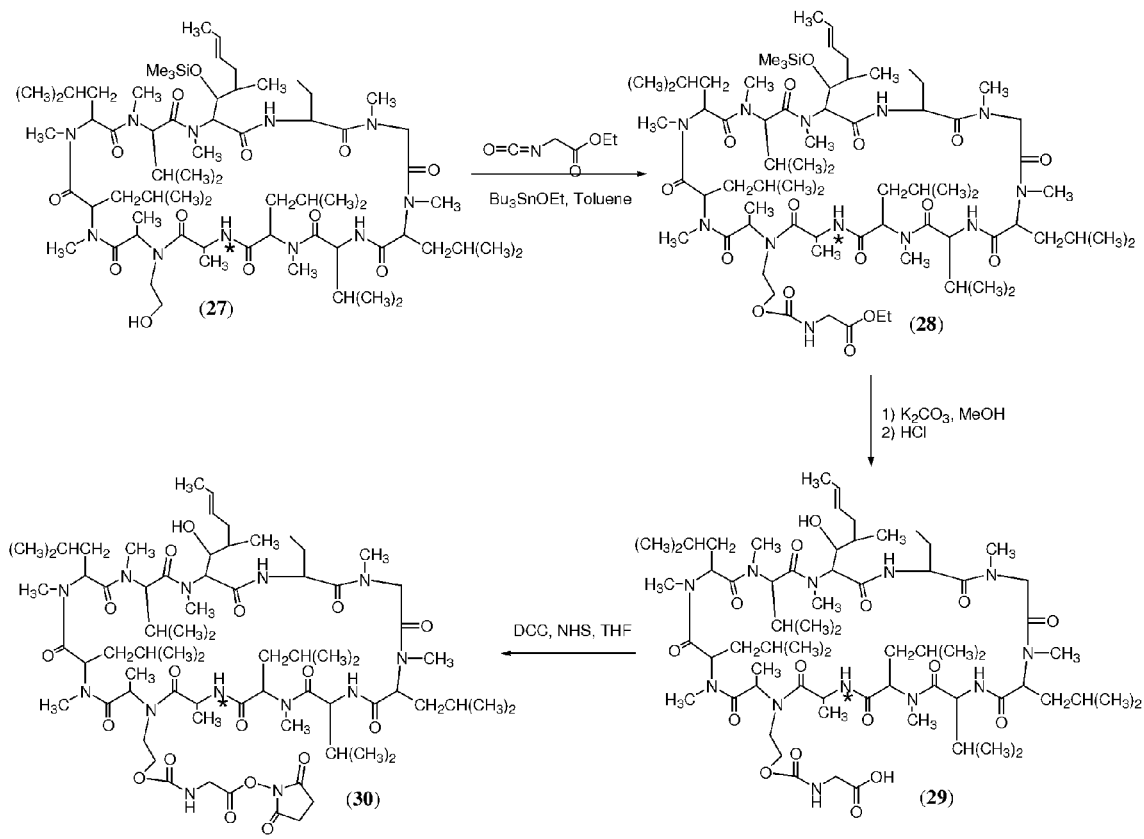
FIG. 12 is a depiction of the preparation of a cyclosporin A intermediate.

The synthesis of 30 is depicted in FIG. 12, Scheme 8. Compound 27 is treated to obtain an activated ester using an activation agent such as, for example, ethyl isocyantoacetate, or the like under conditions appropriate for the activation agent. For example, with ethyl isocyantoacetate as the activation agent, the reaction is carried out under tributyltin ethoxide in toluene at a temperature of about 0 to about 40° C., for a period of about 2 to about 16 hours, to give ester (28). Hydrolysis of the ethyl ester and de-protecting of the silicon protecting group on 28 is achieved in a one-step reaction to give acid (29) by treatment under basic conditions such as, for example, sodium carbonate, potassium carbonate, sodium hydroxide, or the like, in an organic solvent such as, for example, an alcohol, e.g., methanol, ethanol, etc., or by treatment under acidic conditions such as, for example, dilute mineral acid as discussed above.

Figure 13:
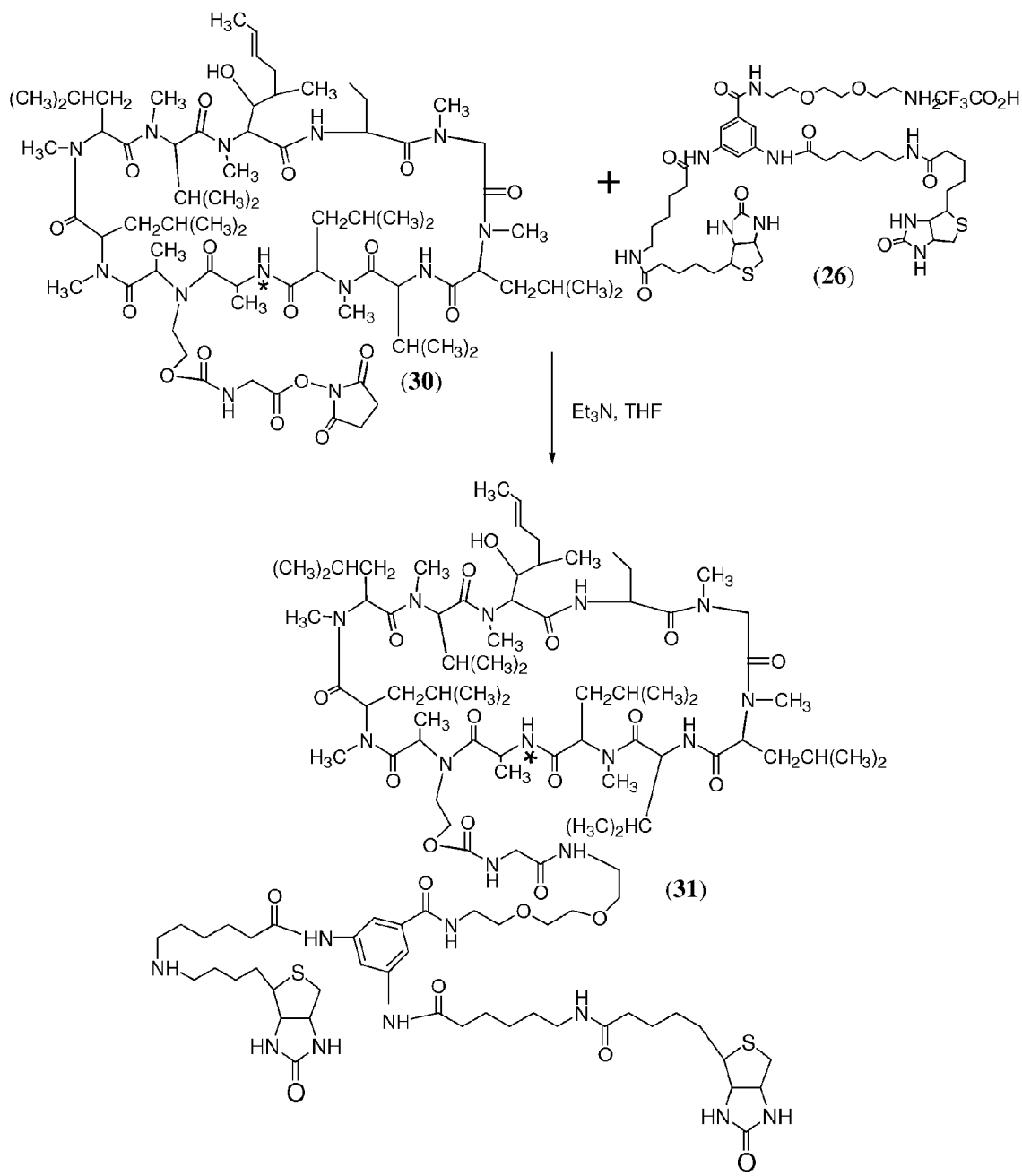
FIG. 13 is a depiction of the preparation of a conjugate of cyclosporin A and bis-biotin.

The acid group on 29 is activated by treatment with an activation agent such as, for example, NHS and DCC, carbodiimide, or the like, in an organic solvent such as, for example, an ether, e.g., THF, DMF, or the like, to give NHS ester (30) (FIG. 12, Scheme 8). The above reaction is carried out at a temperature of about 0 to about 40° C., for a period of about 3 to about 16 hours. The coupling reaction of 30 with 26 is carried out under basic conditions such as, for example, triethyl amine, diisopropyl ethyl amine, or the like in an organic solvent such as, for example, an ether, e.g., THF, DMF, dichloromethane, or the like to give final product, CsA-Bis-Biotin (31) (FIG. 13, Scheme 9). The coupling reaction is carried out at a temperature of about 0 to about 40° C., for a period of about 4 to about 16 hours at a pH of about 9 to about 11.

Kits Comprising Reagents for Conducting Assays for an Analyte

The reagents for conducting a particular assay may be present in a kit useful for conveniently performing an assay for the determination of an analyte. In some embodiments a kit comprises in packaged combination a dry assay reagent as described above as well as any other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional sbp members, ancillary reagents, and so forth.

The relative amounts of the various reagents in the kits can be varied widely to provide for concentrations of the reagents that substantially optimize the reactions that need to occur during the present method and further to optimize substantially the sensitivity of the assay. The kit can further include a written description of a method in accordance with the present invention as described above.

EXAMPLES

General Comments

Analytical thin layer chromatography (TLC, silica) is the usual analysis method and was performed using plates from Analtech, Inc. (Newark, Del.) with the solvent specified below. The spots on TLC were visualized by ultraviolet light (short and/or long wave) and/or iodine vapors. Preparative thin layer chromatography (PTLC) separations were carried out on pre-coated silica gel plates from Whatman Inc. (Clifton, N.J.) and Analtech Inc. Flash chromatography was carried out on Whatman silica gel 60 Å (230-400 mesh) (Whatman Inc., Florham Park, N.J.). The reagents and solvents were commercial grades and used without further purification. Sirolimus (Rapamycin) was obtained from BioAge Pharmaceuticals Inc., San Diego, Calif. FK-506-CMO (11) was obtained from the Glasgow Site, Siemens Medical Solutions Diagnostics. Unless otherwise specified, reagents were obtained from Sigma Chemical Company (St. Louis Mo.), Aldrich Chemical Company (Milwaukee Wis.), or Fluka Chemical Corporation (Milwaukee Wis.) and used as received. The streptavidin-sensitizer bead was prepared in a method analogous to that described in U.S. Pat. Nos. 6,153,442, 7,022,529 and 7,229,842, the relevant disclosures of which are incorporated herein by reference. Assays were conducted using the DIMENSION® RxL analyzer available from Dade Behring Inc., Newark Del. The instrument was employed using induced luminescence immunoassay technology and was equipped with an appropriate reader.

Preparation of Compounds

Figure 2:
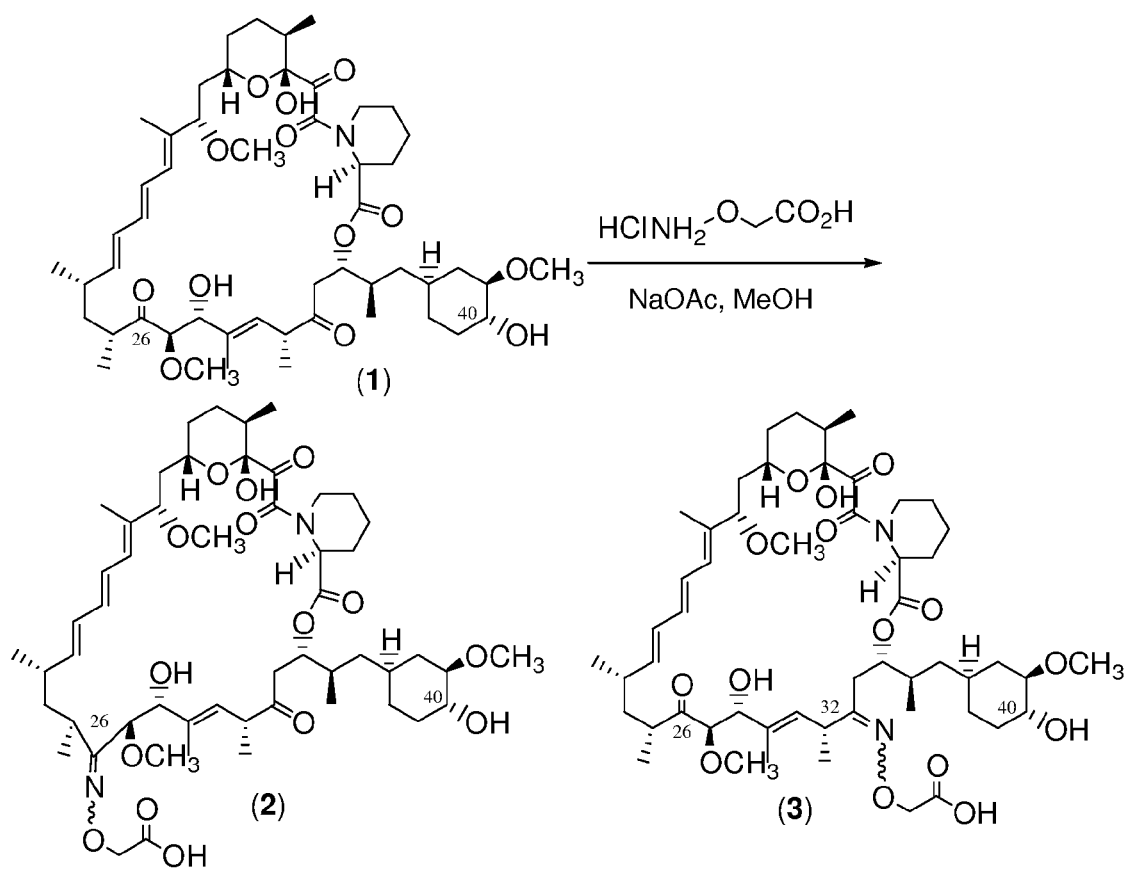
FIG. 2 is a depiction of Scheme 1, preparation of Compounds (2) and (3).

Preparation of Compounds (2) and (3) (see FIG. 2, Scheme 1). To a solution of sirolimus (1) (1 g, 1.0545 mmol) and carboxymethyoxyamine hemihydrochloride (CMO) (823 mg, 3.16 mmol) in methanol (MeOH) (41 mL), was added sodium acetate (263.0 mg, 3.18 mmol). The reaction mixture was stirred at room temperature under nitrogen atmosphere overnight and the progress of the reaction was monitored by TLC (silica gel) (MeOH/$CH_2Cl_2$=1/9) (MeOH is methanol). De-ionized water (40 mL) and methylene chloride (40 mL)

were added into the mixture. The aqueous layer was extracted with methylene chloride (3×40 mL) and the combined organic layers were then washed with de-ionized water (20 mL), dried over $Na_2SO_4$, filtered and concentrated. This gave crude product (1.0774 g). Purification of the crude product (148.8 mg) with three preparative TLC plates (silica gel, 150 A°, 1000 µm, Whatman) (ethyl acetate (EtOAc)/Hexane/ MeOH)=5/2/1) was performed to give two compounds (2) (32.6 mg, 45% yield) and (3) (39.4 mg, 55%). (2).

Figure 3:
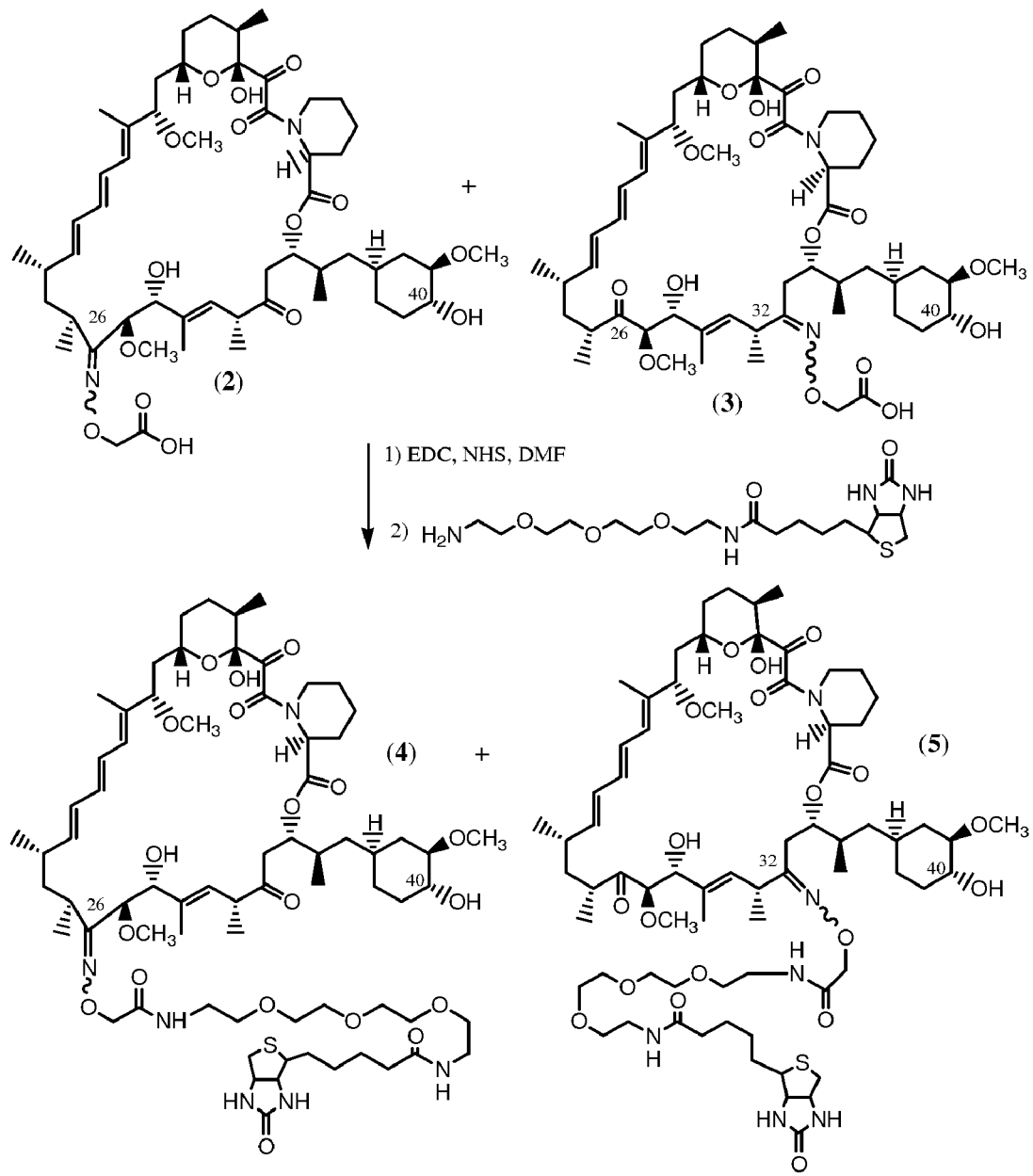
FIG. 3 is a depiction of Scheme 2, preparation of Rapa-C26/C32-PEO$_4$-Biotin Compounds (4) and (5).

Preparation of Rapa-C26/C32-$PEO_4$-Biotin Compounds (4) and (5) (see FIG. 3, Scheme 2). To a solution of compounds (2, 3) (50 mg, 0.05065 mmol) in tetrahydrofuran (THF) (5 mL) were added N-hydroxysuccinimide (NHS) (26 mg, 0.226 mmol) and N,N-dicyclohexyl carbodiimide (DCC) (50 mg, 0.2422 mmol). The reaction mixture was stirred at room temperature for 16 hours and the product rapamycin (Rapa)-NHS ester was a spot less polar than compound (2, 3). The progress of the reaction was monitored by TLC (silica gel, $CH_2Cl_2$/MeOH=1/9). White solid formed during the reaction and was filtered off and the THF filtrate was added with diisopropyl ethyl amine (DIPEA) (0.06 ml) and a solution of Biotin-PEO-LC-Amine (Pierce Chemical Company, Rockford, Ill. 61105) (50 mg, 0.119 mmol) in dimethylformamide (DMF) (3 ml). The reaction mixture was stirred at room temperature for 2 hours. Most of THF and DMF were removed by rotary evaporation under high pressure. The residue was dissolved in $CH_2Cl_2$ (0.5 ml) and the resulting solution was applied to a preparative TLC plates (silica gel, 2000 µm, 20 cm×20 cm, Analtech). Purification of the crude product with PTLC plates ($CH_2Cl_2$/MeOH=1/9) was performed to give the desired two isomers (4) and (5) (48 mg): HPLC analysis of isomers showed that the molar ratio of (4) to (5) is 1 to 1.5.

Figure 4:
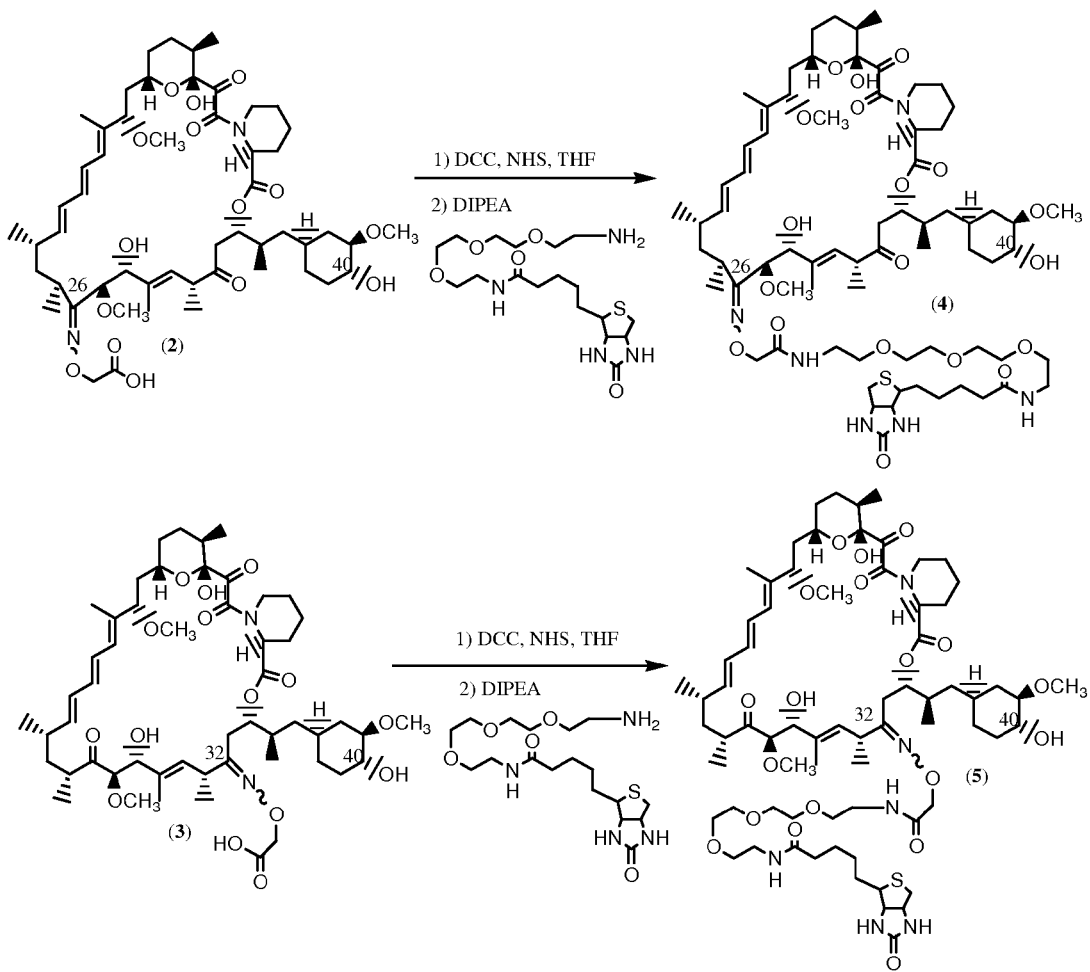
FIG. 4 is a depiction of Scheme 3, preparation of Rapa-C26-PEO$_4$-Biotin (4) and preparation of Rapa-C32-PEO$_4$-Biotin (5).

Preparation of Rapa-C26-$PEO_4$-Biotin (4) (see FIG. 4, Scheme 3). To a solution of (2) (12 mg, 0.0122 mmol) in THF (2 mL) were added N-hydroxysuccinimide (NHS) (6 mg, 0.052 mmol) and N,N-dicyclohexyl carbodiimide (DCC) (8 mg, 0.0387 mmol). The reaction mixture was stirred at room temperature for 16 hours and the product rapamycin (Rapa)-NHS ester was a spot less polar than compound (2). The progress of the reaction was monitored by TLC (silica gel, $CH_2Cl_2$/MeOH=1/9). White solid formed during the reaction and was filtered off and the THF filtrate was added with DIPEA (0.02 ml) and a solution of Biotin-PEO-LC-Amine (15 mg, 0.035 mmol) in DMF (0.3 ml). The reaction mixture was stirred at room temperature for 2 hours. Most of the THF and DMF were removed by rotary evaporation under high pressure. The residue was dissolved in $CH_2Cl_2$ (0.2 ml) and the resulting solution was applied to a preparative TLC plates (silica gel, 2000 µm, 20 cm×20 cm, Analtech). Purification of the crude product with PTLC plates ($CH_2Cl_2$/MeOH=9/1) was performed to give the pure isomers (4) (5.2 mg). HPLC analysis of 4 showed it has a retention time of 3.6 minutes.

Preparation of Rapa-C32-$PEO_4$-Biotin (5) (see FIG. 4, Scheme 3). To a solution of (3) (39 mg, 0.05065 mmol) in THF (3 mL) were added N-hydroxysuccinimide (NHS) (12 mg, 0.104 mmol) and N,N-dicyclohexyl carbodiimide (DCC) (22 mg, 0.106 mmol). The reaction mixture was stirred at room temperature for 16 hours and the product rapamycin (Rapa)-NHS ester is a spot less polar than compound (3). The progress of the reaction was monitored by TLC (silica gel, $CH_2Cl_2$/MeOH=1/9). White solid, which formed during the reaction, was filtered off and the THF filtrate was added with DIPEA (0.04 ml) and a solution of Biotin-PEO-LC-Amine (40 mg, 0.095 mmol) in DMF (0.4 ml). The reaction mixture was stirred at room temperature for 2 hours. Most of the THF and DMF were removed by rotary evaporation under high pressure. The residue was dissolved in $CH_2Cl_2$ (0.4 ml) and the resulting solution was applied to a preparative TLC plates (silica gel, 2000 µm, 20 cm×20 cm, Analtech). Purification of the crude product with PTLC plates ($CH_2Cl_2$/MeOH=9/1) was performed to give the pure isomer (5) (40 mg): HPLC analysis of 5 showed that it has a retention time of 2.6 minutes. Mass spectrum for formula: $C_{71}H_{114}N_6O_{19}S$ (5) (FAB; m/e: $MNa^+$, 1409.9).

Figure 5:
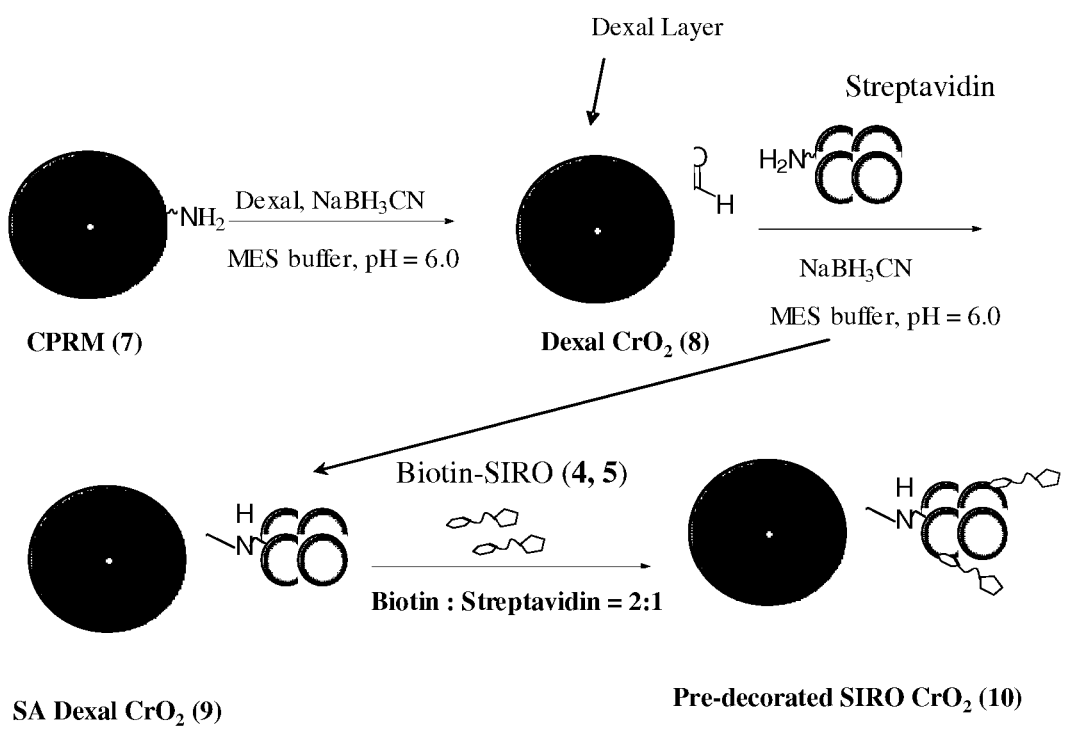
FIG. 5 is a depiction of the preparation of Preformed Siro-Dexal-Chromium dioxide (10).

Preparation of Preformed Siro-Dexal-Chromium dioxide (10) (see FIG. 5, Scheme 4). CPRM (7) (prepared as described in U.S. Pat. No. 4,661,408, the relevant disclosure of which is incorporated herein by reference) (120 mL) was combined with MES buffer solution (50 mM, pH 6.0; 3×200 mL) at 6000 rpm for 2 minutes and re-suspended to a total volume of 120 mL with the same buffer. The CPRM was centrifuged at 3500 rpm for 12 minutes after each wash. Dexal solution (180 mL) was added to the CPRM (120 ml) and the resulting slurry was shaken at ambient temperature for 20 minutes and the pH was adjusted to 6.0 with 1N HCl if necessary. Sodium cyanoborohydride (614 mg) was dissolved in 2 mL of deionized water and adjust with the deionized water to total volume of 3 ml. The resulting solution (3 mL) was added dropwise to the mixture (120 ml CPRM+180 ml dexal) while swirling and the reaction mixture was rocked using an ADAMS® Nutator at ambient temperature for 64±4 hours over the weekend. Dexal-chrome was centrifuged at 3500 rpm for 12 minutes and the supernatant was removed. The dexal-chrome was re-suspended phosphate buffer (200 ml, pH=7, 100 mM) and washed at 6000 rpm for 2 minutes (L4RT-W® Mixer (Silverson Machines Inc., East Longmeadow Mass.). The dexal-chrome was centrifuged at 3500 rpm for 12 minutes and the supernatant was removed. The entire process was repeated with the dexal-chrome with phosphate buffer (100 mM, pH =7, 4×200 ml), deionized water (5×200 mL) and then MES buffer (5×200 ml, 50 mM, pH=6.0). The dexal chromium dioxide product (8) was suspended in 100 mL of the same MES buffer for the next reaction.

Streptavidin (SA) (1200 mg, lyophilized powder, 70% purity) was dissolved in 12 mL deionized water and added to the dexal chromium dioxide product (8) (chrome) slurry (100 ml) from above. The mixture was rocked at ambient temperature for 20 minutes. Sodium cyanoborohydride (300 mg) was dissolved in deionized water (8 mL) and the sodium cyanoborohydride solution was added dropwise to the dexal chromium dioxide product (8) (100 ml) while swirling. The reaction mixture was rocked at 37° C. for 64±4 hours over the weekend. 1M CMO solution (1.2 ml) was added to the chrome and mixture was rocked at 37° C. for 2 hours. The SA-dexal chromium dioxide product (9) was centrifuged at 3500 rpm for 12 minutes and the supernatant was removed. The SA-dexal chromium dioxide product (9) was resuspended in phosphate buffer (200 ml, pH=7.0, 100 mM) and washed (L4RT-W® Mixer) at 6000 rpm for 2 minutes and then centrifuged at 3500 rpm for 12 minutes and the supernatant was removed. The entire process was repeated with the phosphate buffer (14×200 ml, pH=7.0, 100 mM) fourteen times. The SA-dexal chromium dioxide product (9) was resuspended to total volume (120 ml) with the same phosphate buffer. In this chrome preparation, $7.53×10^{-9}$ mole (SA)/ml (5% chrome solid) was detected.

Sirolimus-biotin (4, 5) (2.1 mg, 0.0015 mmol) was dissolved in MeOH (0.5 ml) and added to phosphate buffer (9.5 ml, pH=7.0, 100 mM). The sirolimus-biotin solution (10 ml) was added dropwise to the SA-dexal chromium dioxide (9) (100 ml, $7.53×10^{-9}$, 0.000753 mmole) while swirling and aluminum foil was employed to protect the mixture from light. The reaction mixture was rocked at ambient temperature for 48±4 hours. The mole ratio of biotin to SA was 2 to 1. The preformed siro-biotin-dexal-chrome was centrifuged at 3500 rpm for 12 minutes and the supernatant was removed. The siro-biotin-dexal-chrome product was resuspended in phosphate buffer (200 ml, pH=7.0, 100 mM) and washed (L4RT-W® Mixer) at 6000 rpm for 2 minutes. The siro-biotin-dexal-chrome was centrifuged at 3500 rpm for 12 minutes and the supernatant was removed. The entire process was repeated with the phosphate buffer (10×200 ml, pH=7.0, 100 mM) and PIPES buffer (5×200 ml, pH=6.50, 50 mM). The resulting product was suspended to total volume (100 ml) with the same PIPES buffer. The total volume was adjusted to 5% to give the preformed siro-biotin::streptavidin-dexal-chromium dioxide (10) (referred to in FIG. 5 as "pre-decorated SIRO $CrO_2$ (10)", which was used to make dry chrome tablets as describe below.

Figure 6:
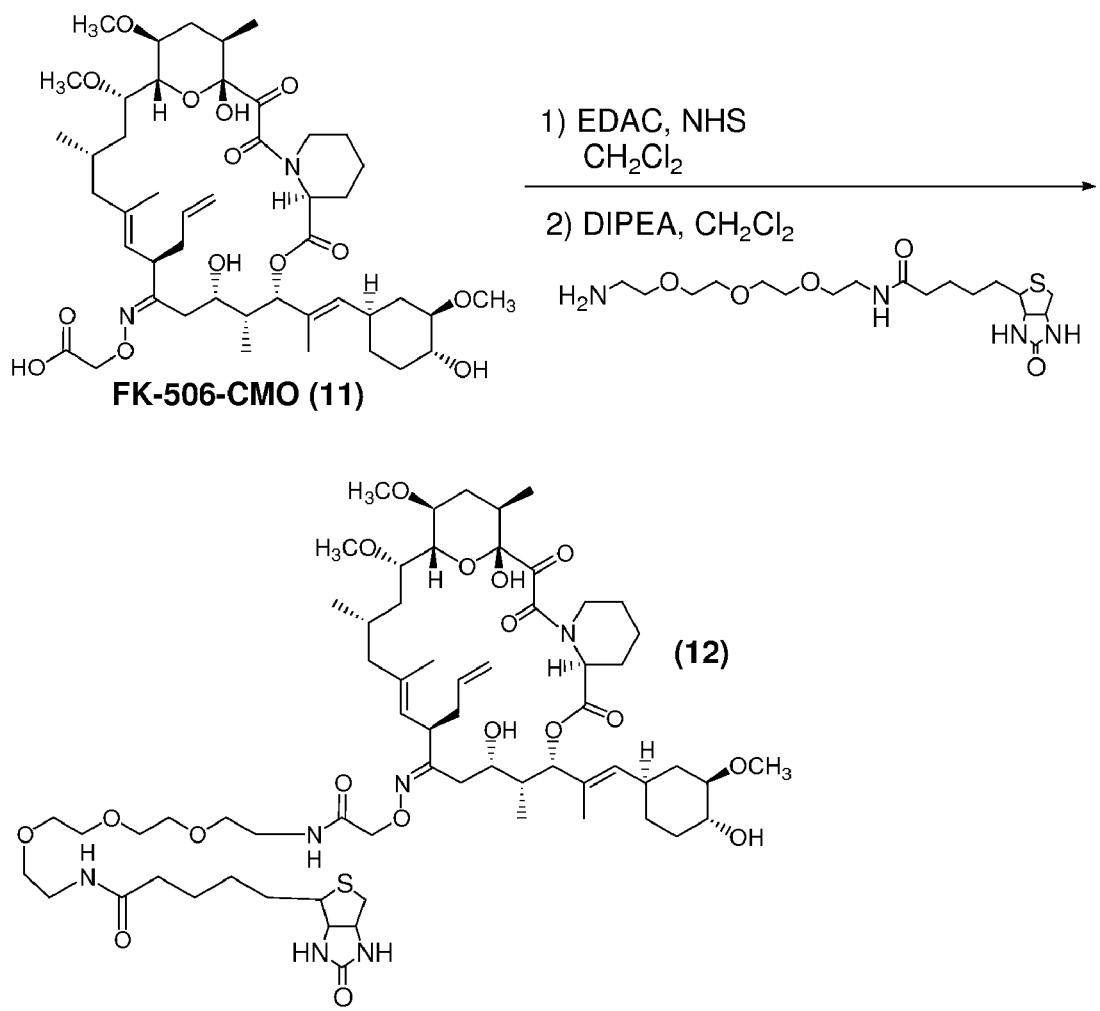
FIG. 6 is a depiction of Scheme 5, preparation of Tacrolimus-PEO$_4$-Biotin (12).
Figure 9:
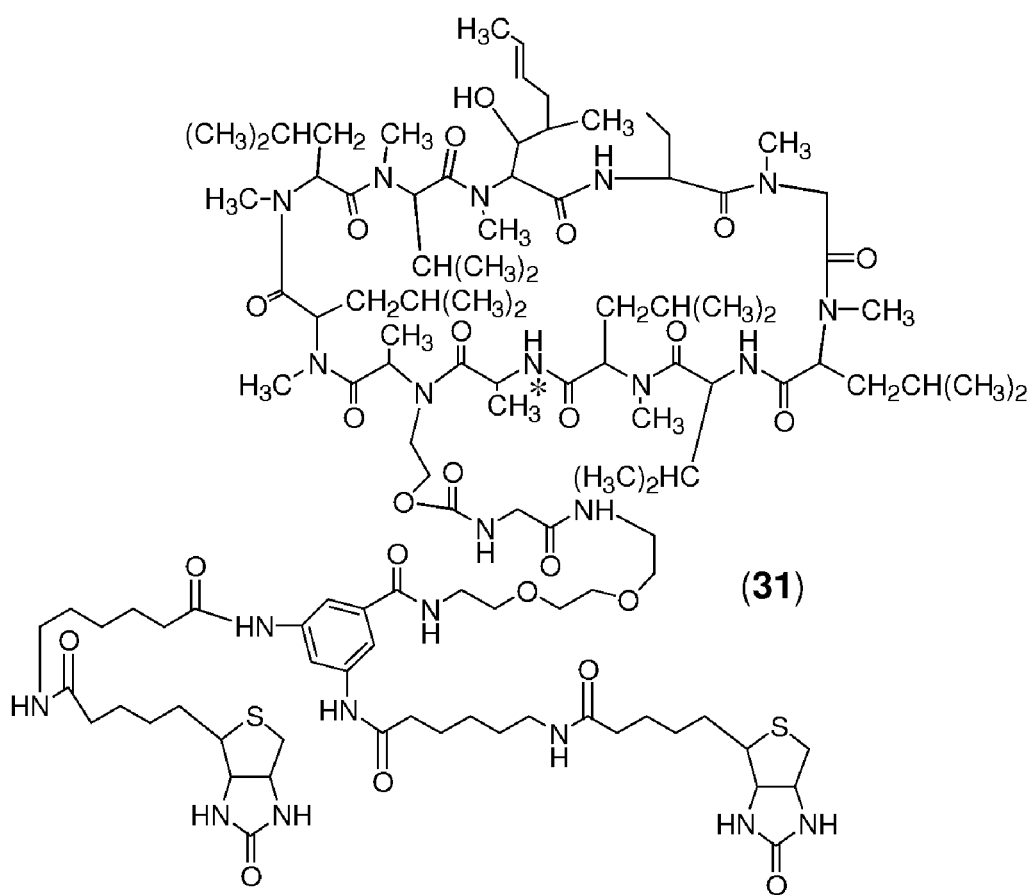
FIG. 9 is a depiction of the structure of a conjugate of cyclosporin A and bis-biotin.

Preparation of Tacrolimus-$PEO_4$-Biotin (12) (see FIG. 6, Scheme 5). To a solution of FK-506-CMO (11) (75 mg, 0.0855 mmol) in THF (5 mL) were added N-hydroxysuccinimide (NHS) (20 mg, 0.173 mmol) and N,N-dicyclohexyl carbodiimide (DCC) (45 mg, 0.218 mmol). The reaction mixture was stirred at room temperature for 16 hours and the product, tacrolimus-NHS ester, was a spot less polar than compound (11). The progress of the reaction was monitored by TLC (silica gel, $CH_2Cl_2$/MeOH=1/9). White solid formed during the reaction was filtered off and the THF filtrate was added with DIPEA (0.02 ml) and a solution of Biotin-PEO-LC-Amine (50 mg, 0.119 mmol) in DMF (0.5 ml). The reaction mixture was stirred at room temperature for 2 hours. Most of THF and DMF were removed by rotary evaporation under high pressure. The residue was dissolved in $CH_2Cl_2$ (0.2 ml) and the resulting solution was applied to a preparative TLC plates (silica gel, 2000 µm, 20 cm×20 cm, Analtech). Purification of the crude product with PTLC plates ($CH_2Cl_2$/MeOH)=9/1) was performed to give the pure isomers (12) (124 mg).

Preparation of biotinylated sirolimus::streptavidin dexal chromium dioxide tablets at 2 (biotin):1 (streptavidin) molar ratio. The core of chromium dioxide particles was first coated with silica and further coated with a silane according to the procedure described in U.S. Pat. No. 4,661,408, the relevant disclosure of which is incorporated herein by reference. The amine groups on silane were then reacted first with dextran aldehyde (MW=500 KD) in MES buffer, pH 6.0 in the presence of $NaBH_3CN$ to form a coated dexal layer on the chrome surface (see scheme 4). The dexal chrome was reacted with streptavidin under the same conditions to form streptavidin-coated chrome as described above. The biotinylated sirolimus made as described above was then incubated in 2:1 molar ratio with streptavidin for 48-64 hrs. The chrome slurry was washed with 100 mM Na phosphate buffer, pH 7.0 for 10 times and then in 50 mM PIPES buffer, pH 6.5 for 5 times. The washed chrome slurry was then let sit for 8 hours or until the supernatant became clear. The supernatant was then carefully removed to harvest the chrome slurry. A solution containing 8% (w/w) carbowax (PEG 8000) and 84% (w/w) trehalose was slowly added to the chrome slurry, which was mixed with a propeller mixer. The solution was mixed for 10 minutes before loading on a spray assembly (U.S. Pat. Nos. 4,712,310, 4,678,812, 3,932,943, 3,721,725, the relevant disclosures of which are incorporated herein by reference). The pressure of liquid nitrogen ($LN_2$) for the Snow-gun was maintained to achieve an output of product temperature within the range of −140° C. to −175° C. (expected $LN_2$ pressure was 22-32 psi). The spray solution was sprayed through egg crate nozzles to form uniform fine droplets (not all are frozen). The droplets were collected and finished to be frozen in a tray, which contained $LN_2$. After the snow-gun spray of the solution was finished, the resultant blend (frozen droplets or granules) were transferred and loaded immediately into a pre-cooled Hull Freeze dryer (<−35° C., SP Industries, Inc, Warminster, Pa.), where it was lyophilized for 5 days until it became dry blend powder. The dried blend powder was then collected and pressed to 30 mg chrome tablets using a single station tablet press (Advanced Machinery, Mich. 48035).

Preparation of Rapamycin-DA10-Dexal-Chrome Slurry. Rapamycin-DA10-dexal-chrome slurry was prepared according to the procedure disclosed in U.S. Pat. No. 7,189,582, the relevant disclosure of which is incorporated herein by reference. The washed chrome slurry suspension was then let sit for 8 hours or until the supernatant became clear. The supernatant was carefully removed to harvest the chrome particles. A solution containing 8% (w/w) carbowax (PEG 8000) and 84% (w/w) trehalose was slowly added to the chrome slurry, which was mixed with a propeller mixer. The solution was mixed for 10 minutes and then freeze dried and formed into tablets as described above.

Preparation of EPRM-anti-CsA-Ab-Chemibead (19). See FIG. 10. To EPRM chemibead suspension (2 ml, 100 mg/ml) was added 2 ml of anti-CsA-Antibody (2G4, IgG1) solution (20 mg/ml) in MES buffer (50 mM, 1 ml, pH=6.0) in a greenroom avoiding daylight. To this suspension was added 0.09 ml of $NaCNBH_3$ (25 mg/ml) solution. The reaction mixture was rocked in an ADAMS Nutator at 37° C. for 63 hours. 1M CMO solution (0.25 mL) was added to the mixture, which was rocked at 37° C. for 2.5 hours. The mixture was centrifuged at 15,000 rpm for 25 minutes and the pellet was re-suspended by sonication with 30 ml of phosphate buffer (50 mM, pH=8.0). The wash process was repeated (13×30 ml) with the same buffer and (5×30 ml) with the suspension buffer (50 mM HEPES, 300 mM NaCl, 1 mM EDTA, 1 mg/ml BSA, 0.1% TX-405, 0.15% Proclin 300, 0.1 mg/ml neomycin sulfate, pH=8.0). The EPRM-anti-CsA-Ab-chemibead (19) was re-suspended in 5 ml of the same suspension buffer and the solid % was determined to be 28.3 mg/ml.

Preparation of compound (23). Compound (23) was prepared by methods similar to those previously described in U.S. Pat. No. 6,153,442.

Preparation of compound (24). Compound (24) was prepared as follows: See FIG. 20. To a solution of (23) (10 g, 40.7 mmol) in THF (100 ml) was added dropwise $Et_3N$ (4.6 g) and 3,5-dinitrobenzoyl chloride (9.2 g, 39.9 mmol) in THF (100 ml). The reaction mixture was stirred at room temperature for 2 hours. Most of the THF was removed by rotary evaporation under reduced pressure. The residue was dissolved in $CH_2Cl_2$ (200 ml) and water (120 ml) was added. The mixture was poured into a separation funnel and extracted with 0.2N HCl (2×100 ml), 0.1 N sodium carbonate (2×50 ml) and water (1×100 ml). The organic phase was dried over sodium sulfate, filtered and evaporated to dryness. The residue was subjected to high vacuum to give the intermediate (15.5 g) as a viscous oil. This intermediate (486 mg, 1.1 mmol) was dissolved in ethanol (EtOH) (30 ml) containing 10% Pd on carbon (400 mg). The mixture was bubbled with nitrogen for 20 minutes to remove oxygen in the solution. To this solution was added sodium borohydride (400 mg) under nitrogen and the mixture was stirred at room temperature for 5 minutes. HCl (1N, 1 ml) was added dropwise into the mixture (Caution: hydrogen was formed from the reaction) under nitrogen in the period of time (10 minutes). The mixture was stirred for 30 minutes. An additional 1 ml of HCl (1N) was added to the mixture, which was stirred for an additional 30 minutes followed by one more addition of 1 ml of HCl (1 N). The mixture was stirred for 120 minutes and bubbled with nitrogen for 10 minutes. The ethanol was filtered with celite and the celite was washed with ethanol (2×10 ml). The combined ethanol was concentrated to dryness and the residue was purified by flash column chromatography (silica gel) using MeOH/$CH_2Cl_2$ (1/9) to give the desired product (24) (264 mg).

Preparation of Compound (25). See FIG. 20. To a solution of 24 (88 mg, 0.23 mmol) in THF (10 ml) was added $Et_3N$ (0.3 mL) and sulfo-NHS-LC-biotin (15) (260 mg, 0.467 mmol). The reaction mixture was stirred at room temperature for 5 hours. Additional sulfo-NHS-LC-biotin (125 mg, 0.224 mmol) and $Et_3N$ (0.15 ml) was added to the mixture. The mixture was stirred for additional 5 hours. Most of the THF was removed by rotary evaporation under reduced pressure. The residue was dissolved in MeOH/$CH_2Cl_2$ (1/9) (0.3 ml) and the solution was applied to a preparative THC plate (Analtech, Catalog No: 02015, silica gel, 2000 µm). The TLC was developed in mixed solvent (MeOH/$CH_2Cl_2$=2/8) and the major band was collected and extracted with (MeOH/$CH_2Cl_2$=3/7) (50 ml). The solvent was evaporated to dryness and the residue was put in high vacuum to give the desired product (25) (39 mg).

Preparation of Compound (26). See FIG. 20. To a solution of compound (25) (39 mg, 0.0367 mmol) in $CH_2Cl_2$ (2 ml) was added trifluoroacetic acid (TFA) (1.5 mL). The reaction mixture was stirred at room temperature for 20 minutes. TLC analysis of the reaction showed that starting material (25) disappeared and a new more polar spot was displayed (silica gel, ethyl acetate). Most of the $CH_2Cl_2$ and TFA were removed by rotary evaporation under reduced pressure. The residue was put in 20 ml of hexane and 15 ml of $CH_2Cl_2$. The solvent was evaporated to dryness again to remove a trace of TFA and the residue was put under high vacuum for 2 hours. This gave the desired product (26) used for next reaction without further purification.

Preparation of CsA Intermediate (28). See FIG. 21. To a solution of compound (27) (240 mg, 0.1819 mmol) in toluene (3 mL) was added tributyltin ethoxide (112 mg, 0.112 ml, 0.0969 mmol) under nitrogen. The reaction was stirred at room temperature for 5 minutes. To this solution was added ethyl isocyanatoacetate (73 µL, 84 mg, 0.652 mmol). The reaction was stirred at room temperature for 2 hours. TLC analysis of the reaction showed that starting material (27) disappeared and a new less polar spot was displayed (silica gel, MeOH/ethyl acetate=3/97). Water (10 ml) was added and the aqueous phase was extracted with ethyl acetate (2×30 ml). The combined organic phase was washed with water (30 ml), brine (30 ml), dried over $Na_2SO_4$, filtered and evaporated to dryness. The residue was purified by flash column chromatography (silica gel) using MeOH/ethyl acetate (3/97) to give the desired product (28) (224 mg).

Preparation of CsA Intermediate (29). See FIG. 21. To a solution of compound (28) (112 mg, 0.0774 mmol) in MeOH (6.0 ml) and $H_2O$ (0.5 ml) was added $K_2CO_3$ (140 mg, 1.01 mmol). The reaction mixture was stirred at room temperature for 16 hours. Water (10 ml) was added and HCl (1N) was added to the mixture to adjust the pH to 1. The reaction mixture was stirred for 10 minutes. The aqueous phase was extracted with $CH_2Cl_2$ (3×30 ml). The combined organic phase was washed with brine/water (1/1) (50 ml). The organic phase was dried over $Na_2SO_4$, filtered and evaporated to dryness. The residue was put in high vacuum for 16 hours. The residue was dissolved at $CH_2Cl_2$/MeOH (2/8) (0.5 ml) and the solution was applied to a preparative THC plate (Analtech, Catalog No: 02015, silica gel, 2000 µm). The TLC was developed in mixed solvent (MeOH/$CH_2Cl_2$=1/9) and the major band was collected and extracted with (MeOH/$CH_2Cl_2$=3/7) (50 ml). The solvent was evaporated to dryness and the residue was put in high vacuum under $P_2O_5$ for 16 hours to give the desired product (29) (55.6 mg).

Preparation of CsA-Bis-Biotin (31). See FIGS. 21-22. To a solution of compound (29) (55.6 mg, 0.04125 mmol) in THF (5 mL) was added DCC (20 mg, 0.0969 mmol) and NHS ester (15 mg, 0.13 mmol). The reaction mixture was stirred at room temperature under argon for 6 hours. TLC analysis of the mixture showed that a less polar spot displayed in comparison with compound (29) (MeOH/$CH_2Cl_2$=1/9). The precipitate from the reaction was filtered off and washed with anhydrous THF (3 ml). The combined organic phase was evaporated to dryness to give activated hapten (30), which was dissolved in DMF (1 ml) for the next reaction.

Compound (26) (FIG. 20) was dissolved in DMF (5 ml) and Et3N (0.1 ml). To this solution was added the activated hapten (30) in DMF solution (1 mL). The reaction was stirred at room temperature for 4 hours. Most of the DMF was removed by rotary evaporation under reduced pressure. The residue was subjected to high vacuum for 2 hours to give crude product (31). The crude product was dissolved in 0.3 ml of MeOH/$CH_2Cl_2$ (1/9) and the solution was applied to two preparative THC plates (Analtech, Catalog No: 02015, silica gel, 2000 µm). The TLC was developed using a mixed solvent (MeOH/$CH_2Cl_2$=1/9) and the major band was collected from two TLC plates and extracted with (MeOH/$CH_2Cl_2$=2/8) (50 ml). The solvent was evaporated to dryness and the residue was put in high vacuum to give the desired product (31) (54 mg).

Preparation of CsA-Bis-Biotin Preformed Sensitizer Beads (34). CsA-Bis-Biotin (31) (1.15 mg) was dissolved in MeOH (0.2 ml) and added into buffer (49.8 ml, 50 mM HEPES, 300 mM NaCl, 1 mM EDTA, 1 mg/ml BSA, 0.1% TX-405, 0.15% Proclin 300, 0.1 mg/ml neomycin sulfate, pH=8.0). This makes a 50 ml of 10 µM of CsA-Bis-Biotin solution. To 5 ml of streptavidin (SA) coated-sensitizer beads (see U.S. Pat. Nos. 6,153,442; 7,022,529; 7,229,842) (1 mg/ml, total SA loading: 3.94 nmole) was added CsA-Bis-Biotin solution. (49.3 µl, 10 µM, 0.493 nmole). The molar ratio of SA to CsA-Bis-Biotin was 1:0.125. The preformed sensitizer bead was incubated at room temperature in a green-room avoiding daylight for 1 hour. The bead was diluted into a total volume of 10 ml with the same buffer to have 0.5 mg/ml bead suspension. The beads were stored at 4° C. This procedure was used to prepare different molar ratios of SA to CsA-Bis-Biotin Preformed Sensitizer Beads (34) for evaluation.

Stability Studies

Comparison of hydrated stability of the preformed chrome tablets with that of the rapamycin-DA10-dexal-chrome in a 64 hour period. The DIMENSION® FLEX® reagent cartridge for the ACMIA sirolimus assay contained four reagents in separate wells, 2.5 mL pretreatment reagent (R1), 1.8 mL anti-sirolimus antibody-β-galactosidase conjugate (R2), four preformed or rapamycin-DA10-dexal-chrome tablets hydrated with 1.9 mL of water (R3) using an ultrasound probe, and 1.8 mL of CPRG solution (R4). Each individual test consumed 70 µL of R1, 50 µL of R2, 50 µL of R3 (chrome) and 155 µL of R4 and the amount of reagent in each well was designated for 10 tests. The extra reagent volume in each well provided the dead volume and also buffered the concentration change due to condensation and evaporation after the wells were punctured by the reagent probe (opened well) and the tablets were hydrated. A linear depletion protocol was employed to conduct the hydrated chrome stability studies. In this protocol, six of the ten tests in each well were used to generate the baseline results at hour 0 using a quality control material (whole blood QC level 2 from More Diagnostics Inc., Los Osos Calif.). After the reagent wells were punctured and the chrome tablets were hydrated for 64 hours, the leftover tests were used to measure sirolimus concentration in the QC material. The FLEX® reagent cartridge containing the preformed chrome tablets share the same other reagents as that containing the rapamycin-DA10-dexal-chrome tablets. Table 1 summarizes a comparison of the QC recoveries using the preformed chrome versus using the rapamycin-DA10-dexal-chrome.

TABLE 1

Hydrated stability comparison
QC recovery of pre-decorated $CrO_2$ vs. rapamycin-DA10-dexal-$CrO_2$

| $CrO_2$ tablets | ng/mL Hr 0 | ng/mL Hr 64 | Δ |
|---|---|---|---|
| PD $CrO_2$ tablets 1967-88 | 11.3 | 10.9 | −0.4 |
| Rapamycin-DA10-Dexal-$CrO_2$ Lot A | 11.3 | 14.2 | 2.9 |
| Rapamycin-DA10-Dexal-$CrO_2$ Lot B | 11.3 | 14.1 | 2.8 |

The results in the above table demonstrate that the hydrated preformed chrome was more stable than the hydrated rapamycin-DA10-dexal-chrome.

Seven-day study of the hydrated stability of the preformed chrome tablets on DIMENSION® VISTA® analyzer. The DIMENSION® VISTA® sirolimus assay employed the same format and principle as used on the DIMENSION® RxL HM modules as described previously. The principle and operation of the sirolimus method on the DIMENSION® VISTA® analyzer were as follows: 32 μL of pretreatment reagent containing the surfactants and a FK506 carbamate compound was added to the reaction vessel on the DIMENSION® chemistry RxL/HM instrument. Next, 8.5 μL of whole blood containing sirolimus was added. The whole blood was sampled from a standard cup by first mixing the blood on board. The mixing of whole blood sample with the pretreatment solution containing the surfactants and FK506 carbamate compound ensured the lysis of the whole blood and the displacement of the protein bound sirolimus molecules from their binding sites by the sirolimus carbamate molecules. Anti-sirolimus antibody-β-galactosidase conjugate (21.5 μL) was added next and allowed to react with sirolimus in the sample. Two-30 mg dry tablets, each containing 2.5 mg of partially preformed chrome particles described previously, 8% (w/w) of trehalose, and 84% (w/w) carbowax (polyethylene glycol 8000), were hydrated with 950 μL of water on board with an ultrasonic reagent probe. Then, 21.5 μL of the hydrated chrome particles was added to the reaction mixture and allowed to bind the unreacted conjugate. The sirolimus bound Anti-sirolimus antibody-β-galactosidase conjugate did not bind to the chrome but remained in the supernatant when a magnetic field was applied to the above reaction mixture to separate the solution from the chrome particles. The sirolimus bound conjugate was detected by transferring the supernatant from the reaction vessel to a photometric cuvette and measuring the enzymatic rate of the conjugate in the presence of CPRG. The rate was measured bichromatically at 577 and 700 nm.

The DIMENSION® VISTA® FLEX® reagent cartridge for the ACMIA sirolimus assay contained four reagents in separate wells, 830 μL of pretreatment reagent (R1), 720 μL of anti-sirolimus antibody-β-galactosidase conjugate (R2), 2 pre-decorated or directly linked chrome tablets hydrated with 950 μL of water (R3) using an ultrasound probe, and 1350 μL of CPRG solution (R4). Each individual test consumed 32 μL of R1, 21.5 μL of R2, 21.5 μL of R3 (chrome) and 60.5 μL of R4 and the amount of reagent in each well was designated for 10 tests. The extra reagent volume in each well is to provide the dead volume and to buffer the concentration change due to condensation and evaporation after the wells are punctured by the reagent probe (opened well) and the tablets are hydrated. A linear depletion protocol was employed to conduct the hydrated chrome stability studies. In this protocol, two human whole blood pools containing approximately 6 and 18 ng/mL of sirolimus were used as testing samples. The tests in each well containing hydrated preformed chrome were linearly depleted on day 0 (3 tests), day 5 (2 tests) and day 7 (3 tests). Table 2 shows the stable recoveries of the two whole blood pools during the 7-day period.

TABLE 2

Hydrated stability of the preformed $CrO_2$ on DIMENSION® VISTA® analyzer

| Day/ng/mL | Day 0 | Day 5 | Day 7 |
|---|---|---|---|
| Pool 1 | 5.9 | 5.4 | 5.6 |
| Pool 2 | 17.2 | 17.0 | 17.7 |

The results in the above table demonstrate good hydrated stability for the preformed chrome over a period of 7 days.

Assays

The following assays were conducted using reagents as described above.

Figure 14:
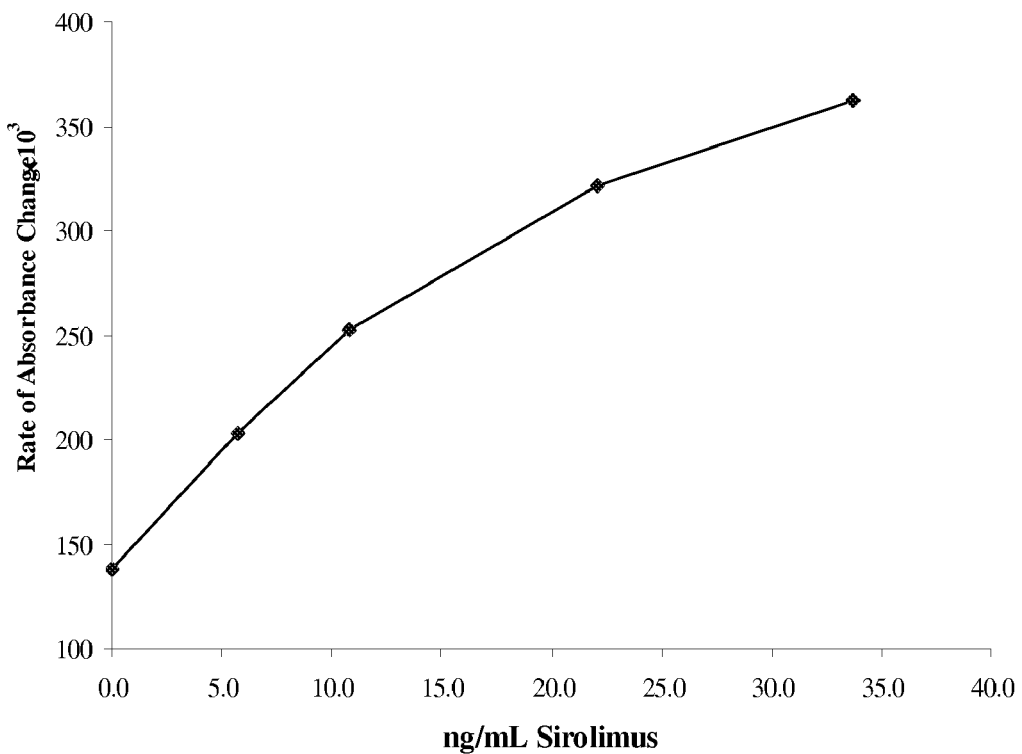
FIG. 14 is a graphic depiction of a typical standard curve for the DIMENSION® sirolimus assay.

Sirolimus Assay. The measurement of sirolimus was carried out using the assay format known as ACMIA. The principle and operation of the sirolimus assay method were as follows: a 70 μL of pretreatment reagent containing the surfactants and a FK506 carbamate compound was added to the reaction vessel on the DIMENSION® chemistry RxL/HM instrument with HM Module. Next, 18 μL of whole blood containing sirolimus was added. The whole blood was sampled from a standard cup by first mixing the blood with the ultrasonic sample probe. The mixing of whole blood sample with the pretreatment solution containing surfactants and FK506 carbamate compound ensured the lysis of the whole blood and the displacement of the protein bound sirolimus molecules from their binding sites by the sirolimus carbamate molecules. Anti-sirolimus antibody-β-galactosidase conjugate (50 μL) is added next and allowed to react with sirolimus in the sample. Four 30 mg dry $CrO_2$ tablets prepared as described above, each containing 2.5 mg of partially preformed chrome particles or the rapamycin-DA10-dexal-chrome particles as described previously, 8% (w/w) of trehalose, and 84% (w/w) carbowax (polyethylene glycol 8000), were hydrated with 1900 μL of water on board with an ultrasonic reagent probe. Then, fifty μL of the hydrated chrome particles was added to the reaction mixture and allowed to bind the unreacted conjugate. The sirolimus bound Anti-sirolimus antibody-β-galactosidase conjugate did not bind to the chrome but remained in the supernatant when a magnetic field was applied to the above reaction mixture to separate the solution from the chrome particles. The sirolimus bound conjugate was detected by transferring the supernatant from the reaction vessel to a photometric cuvette and measuring the enzymatic rate of the conjugate in the presence of chlorophenol red-β-D-galactopyranoside (CPRG). The rate was measured bichromatically at 577 and 700 nm. A typical standard curve for the DIMENSION® sirolimus assay is depicted in FIG. 14.

Cyclosporin A Assay. In this embodiment the amount of CsA in a medium suspected of containing CsA was determined. A combination was provided in a medium wherein the combination comprises (i) the sample, (ii) a preformed reagent comprising a photosensitizer associated with a first particle and being capable of generating singlet oxygen wherein the first particle comprises a biotin-binding partner bound to biotin as part of a conjugate of cyclosporin A and biotin, and (iii) a chemiluminescent composition activatable by singlet oxygen and associated with a second particle wherein the second particle comprises an antibody for cyclosporin A. The combination was subjected to conditions for binding of cyclosporin A to the antibody for cyclosporin A. The photosensitizer was irradiated with light and the amount of luminescence generated by the chemiluminescent composition was detected, the amount of luminescence being related to the amount of cyclosporin A in the sample.

Figure 15:
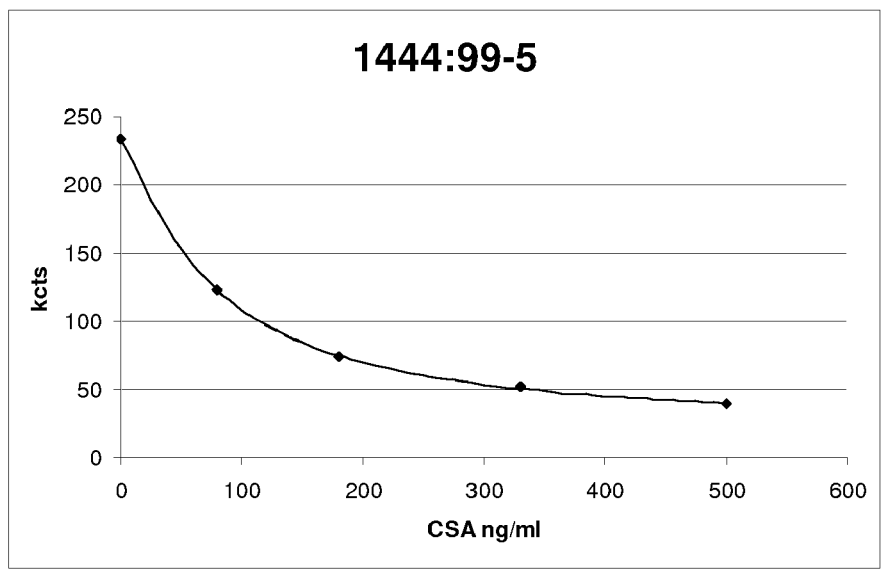
FIG. 15 is graphic depiction of the results of another assay for CsA of the present embodiments using the following reagents: antibody for CsA-chemiluminescent particles and a preformed reagent comprising CsA-bis-biotin and streptavidin-sensitizer particles.

For the above cyclosporin A assay, the following reagents discussed above were employed: CsA-bis-biotin-streptavidin-photosensitizer beads as a preformed reagent (34) and anti-CsA Mab-chemibeads (19). The samples were calibrators 1-5 as discussed above. The appropriate reagents and samples were added to a reaction vessel of the DIMENSION RxL analyzer as follows: Into the reaction vessel, 20 µL of anti-CSA (2G4) Mab-chemibeads was added followed by 20 µL of diluent (50 mM HEPES pH 7.2, 300 mM NaCl, 1 mM EDTA, 1 mg/mL Dextran T-500, 0.1% TRITON x-405, 0.15% Proclin 300, 0.1% Neomycin) followed by 15 µL of water. Then, 10 µL of sample was added followed by 15 µL of water. The combination was incubated for 219 seconds and 20 µL CsA-bis-biotin-streptavidin-photosensitizer beads (31) was added followed by 150 µL of water. The combination was incubated for either 366 seconds or 713 seconds at a temperature of 37° C. Then, the combination was irradiated with light at 680 nM for a period of 0.2 to 1 second and the signal (in photon counts referred to as LOCI signal in the tables below) was read using a reader (Perkin-Elmer CPM Detector). The results are summarized below in Table 3 and in FIG. 15.

TABLE 3

CsA-bis-biotin-streptavidin-photosensitizer beads (34)

| Calibrator | LOCI Signal |
| --- | --- |
| 0.00 | 234 |
| 80.00 | 123 |
| 180.00 | 71 |
| 330.00 | 48 |
| 500.00 | 36 |

As can be seen from the above data, the amount of signal and a sufficient difference between the signal for calibrator 1 (0.00 ng/mL CsA) and calibrator 2 (80.00 ng/mL CsA) is obtained with the preformed reagent. This results in good sensitivity in the medical decision range as discussed above.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A dry assay reagent, said reagent comprising a solid support and one or more molecules of a receptor immobilized on the solid support wherein the receptor comprises one or more binding sites for a ligand and wherein a portion of a total number of the binding sites is bound to a conjugate comprising the ligand covalently linked to a specific binding pair member and a portion of the total number of the binding sites is free.

2. The reagent according to claim 1 wherein the molar ratio of the total number of binding sites to ligand is greater than 1.

3. The reagent according to claim 1 wherein the molar ratio of the total number of binding sites to ligand is 1.5 to 4.

4. The reagent according to claim 1 wherein the receptor is a receptor for a small molecule.

5. The reagent according to claim 4 wherein the small molecule is biotin, dinitrophenol, digoxigenin, fluorescein, a hormone, or a single-stranded nucleic acid chain.

6. The reagent according to claim 1 wherein the solid support is a particle.

7. The reagent according to claim 6 wherein the particle is a magnetic particle.

8. A method for determining the presence and/or amount of an analyte in a sample suspected of containing the analyte, the method comprising:
   (a) providing in combination in an aqueous medium the sample and reagents for detecting the analyte wherein at least one of the reagents comprises the dry assay reagent of claim 1 wherein the specific binding pair member is a binding partner for the analyte or an analyte analog,
   (b) incubating the combination under conditions for binding of the analyte to one or more of the reagents, and
   (c) detecting the presence and/or amount of binding of the analyte to one or more of the reagents, the presence and/or amount of the binding being related to the presence and/or amount of the analyte in the sample.

9. A dry assay reagent, said reagent comprising a particulate solid support and one or more molecules of a biotin-binding partner immobilized on the particulate solid support wherein a portion of a total number of binding sites of the biotin-binding partner is bound to a conjugate comprising biotin covalently linked to a specific binding pair member and a portion of the total number of binding sites is free.

10. The reagent according to claim 9 wherein the molar ratio of the total number of the binding sites to biotin is greater than 1.

11. The reagent according to claim 9 wherein the molar ratio of the total number of the binding sites to biotin is 1.5 to 4.

12. The reagent according to claim 9 wherein the particle is a magnetic particle.

13. The reagent according to claim 9 wherein the biotin-binding partner is streptavidin.

14. A method for determining the presence and/or amount of an analyte in a sample suspected of containing the analyte, the method comprising:
   (a) providing in combination in an aqueous medium the sample and reagents for detecting the analyte wherein at least one of the reagents comprises the dry assay reagent of claim 9,
   (b) incubating the combination under conditions for binding of the analyte to one or more of the reagents, and
   (c) detecting the presence and/or amount of binding of the analyte to one or more of the reagents, the presence and/or amount of the binding being related to the presence and/or amount of the analyte in the sample.

15. The method according to claim 14 wherein the specific binding pair member is an analyte analog.

16. The method according to claim 14 wherein the specific binding pair member is an antibody for the analyte.

17. The method according to claim 15 wherein the reagents include a conjugate comprising an antibody for the analyte linked to an enzyme.

\* \* \* \* \*